US011612377B2

(12) United States Patent
Glaenzer et al.

(10) Patent No.: US 11,612,377 B2
(45) Date of Patent: Mar. 28, 2023

(54) IMAGE GUIDED SURGICAL METHODOLOGY AND SYSTEM EMPLOYING PATIENT MOVEMENT DETECTION AND CORRECTION

(75) Inventors: Mark D. Glaenzer, Saint Louis, MO (US); Robert A. Whitman, Saint Louis, MO (US); Bruce A. Olson, St. Louis, MO (US)

(73) Assignee: Best Medical International, Inc., Springfield, VA (US)

( * ) Notice: Subject to any disclaimer, the term of this patent is extended or adjusted under 35 U.S.C. 154(b) by 0 days.

(21) Appl. No.: 12/970,060

(22) Filed: Dec. 16, 2010

(65) Prior Publication Data

US 2012/0157841 A1     Jun. 21, 2012

(51) Int. Cl.
*A61B 8/12*         (2006.01)
*A61B 8/00*         (2006.01)
(Continued)

(52) U.S. Cl.
CPC .............. *A61B 8/12* (2013.01); *A61B 8/4254* (2013.01); *A61B 8/445* (2013.01); *A61B 8/463* (2013.01); *A61B 8/5223* (2013.01); *A61B 10/0241* (2013.01); *A61B 34/25* (2016.02); *A61B 90/11* (2016.02); *A61B 90/37* (2016.02); *G06T 7/0016* (2013.01); *G06T 7/248* (2017.01);
(Continued)

(58) Field of Classification Search
CPC ......... G06T 7/0012–0016; G06T 7/248; G06T 2207/30081; A61B 10/0241; A61B 2018/00547; A61B 5/11; A61B 5/1107; A61B 5/1114; A61B 5/743; A61B 8/445; A61B 8/463; A61B 8/465; A61B 8/469; A61B 8/5292; A61B 2034/2063
USPC ........ 600/437, 439, 440, 459, 462; 382/128, 382/286–289, 291; 345/619, 629, 634, 345/635; 715/700, 702
See application file for complete search history.

(56) References Cited

U.S. PATENT DOCUMENTS 5,592,942 A    1/1997  Webler et al.
5,954,670 A    9/1999  Baker
(Continued)

OTHER PUBLICATIONS

Bax et al., "3D Transrectal Ultrasound Prostate Biopsy using a Mechanical Imaging and Needle-Guidance System", Proc. of SPIE, vol. 6918, Medical Imaging 2008, 12 pages (Year: 2008).*
(Continued)

*Primary Examiner* — James M Kish

(57) ABSTRACT

A method and system utilizes an imaging device that generates images of target tissue of a patient during a surgical procedure that acts on the target tissue imaged by the imaging device. The method and system enables visual detection of patient movement during the surgical procedure by marking at least one spatial attribute of one or more identifiable features of the target tissue illustrated in an image presented in a display window. Prior to acting on the target tissue, a visual indicator of the spatial attribute(s) is superimposed on one or more subsequent images captured by the imaging device and displayed to the operator. The operator can visually compare a position of the visual indicator to a position of the operator-identified feature in order to detect movement of the patient during the procedure. The system and methodology also facilitates realignment that corrects for detected patient movement.

28 Claims, 28 Drawing Sheets

(51) Int. Cl.
*A61B 8/08* (2006.01)
*A61B 90/11* (2016.01)
*G06T 7/00* (2017.01)
*A61B 10/02* (2006.01)
*G06T 7/246* (2017.01)
*A61B 90/00* (2016.01)
*A61B 34/00* (2016.01)
*A61B 18/00* (2006.01)
*A61B 18/02* (2006.01)
*A61B 18/20* (2006.01)

(52) U.S. Cl.
CPC ....... *A61B 8/467* (2013.01); *A61B 2010/0225* (2013.01); *A61B 2018/00547* (2013.01); *A61B 2018/0293* (2013.01); *A61B 2018/2005* (2013.01); *A61B 2090/378* (2016.02); *G06T 2207/10132* (2013.01); *G06T 2207/20104* (2013.01); *G06T 2207/30081* (2013.01)

(56) References Cited

U.S. PATENT DOCUMENTS

| | | | |
|---|---|---|---|
| 6,004,271 | A | 12/1999 | Moore |
| 6,200,269 | B1 | 3/2001 | Lin et al. |
| 6,709,397 | B2 | 3/2004 | Taylor |
| 7,835,557 | B2 | 11/2010 | Kendrick et al. |
| 8,369,592 | B2 | 2/2013 | Leroy et al. |
| 8,702,579 | B2 | 4/2014 | Bauman et al. |
| 2003/0112922 | A1* | 6/2003 | Burdette ............ A61B 8/4245 378/65 |
| 2004/0034297 | A1* | 2/2004 | Darrow et al. ............... 600/407 |
| 2005/0159676 | A1* | 7/2005 | Taylor ............... A61B 10/0266 600/567 |
| 2007/0010805 | A1* | 1/2007 | Fedewa ................... A61N 7/02 606/27 |
| 2007/0038112 | A1 | 2/2007 | Taylor et al. |
| 2007/0043293 | A1* | 2/2007 | Jones et al. ................... 600/446 |
| 2008/0146933 | A1 | 6/2008 | Lewis et al. |
| 2009/0182312 | A1 | 7/2009 | Gertner et al. |
| 2009/0318804 | A1 | 12/2009 | Avital et al. |
| 2011/0081063 | A1* | 4/2011 | Leroy ................. A61B 8/0841 382/131 |
| 2011/0082363 | A1* | 4/2011 | Xu ....................... A61B 8/4254 600/411 |
| 2012/0203095 | A1* | 8/2012 | Krieger ................. A61B 5/055 600/411 |
| 2013/0090554 | A1* | 4/2013 | Zvuloni ............ A61B 10/0241 600/424 |

OTHER PUBLICATIONS

Transrectal Ultrasonography (TRUS) of the Prostate, Sugandh Shetty, MD., emedicine, May 2008.
U.S. Appl. No. 12/834,357, filed Jul. 12, 2010, Michael O'Laughlin.
U.S. Appl. No. 12/834,384, filed Jul. 12, 2010, Michael O'Laughlin et al.
U.S. Appl. No. 11/895,228, filed Aug. 23, 2007, James D. Taylor et al.
U.S. Appl. No. 11/475,674, filed Jun. 26, 2006, James D. Taylor et al.
PCT/US2011/063226 International Search Report.

* cited by examiner

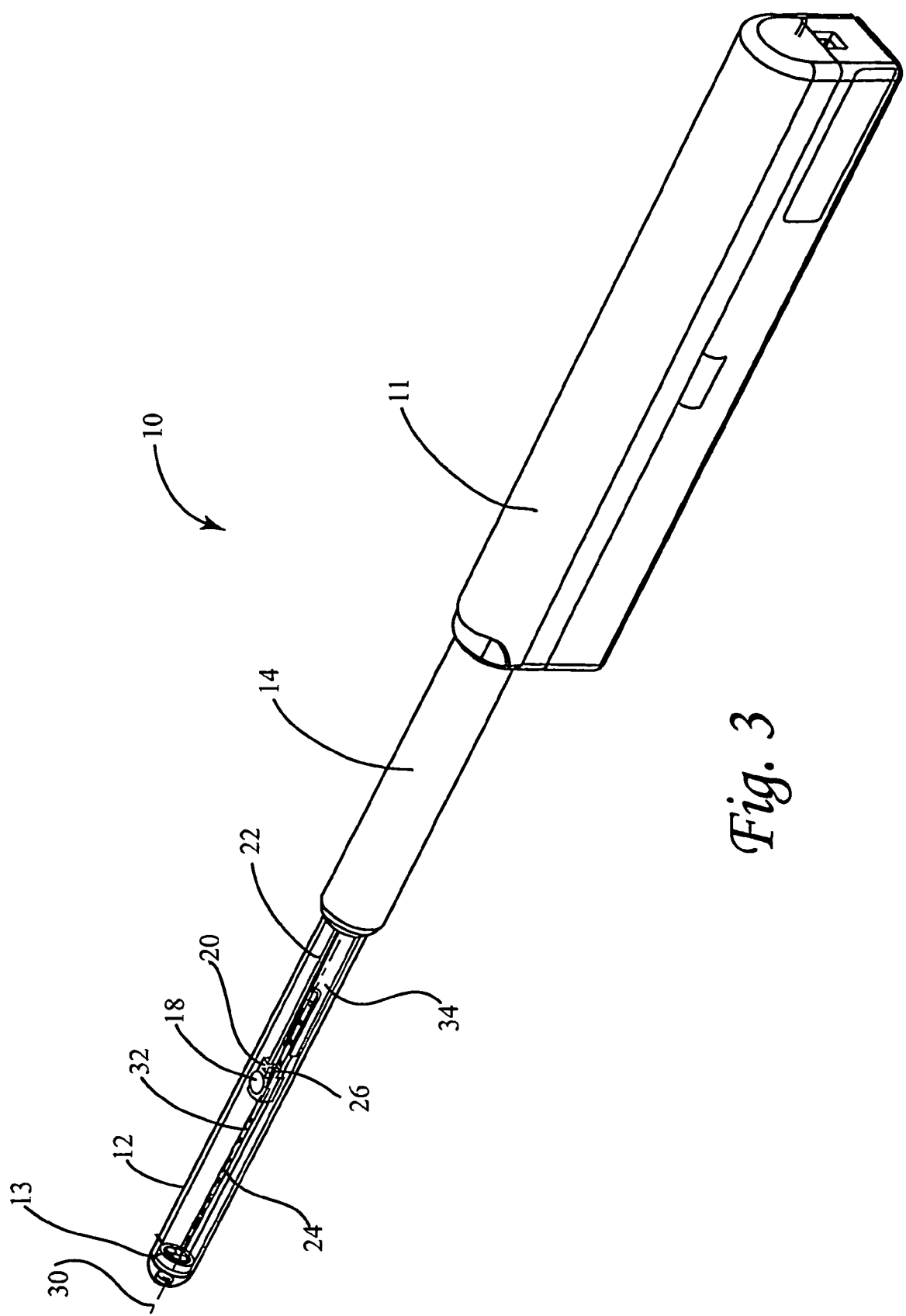

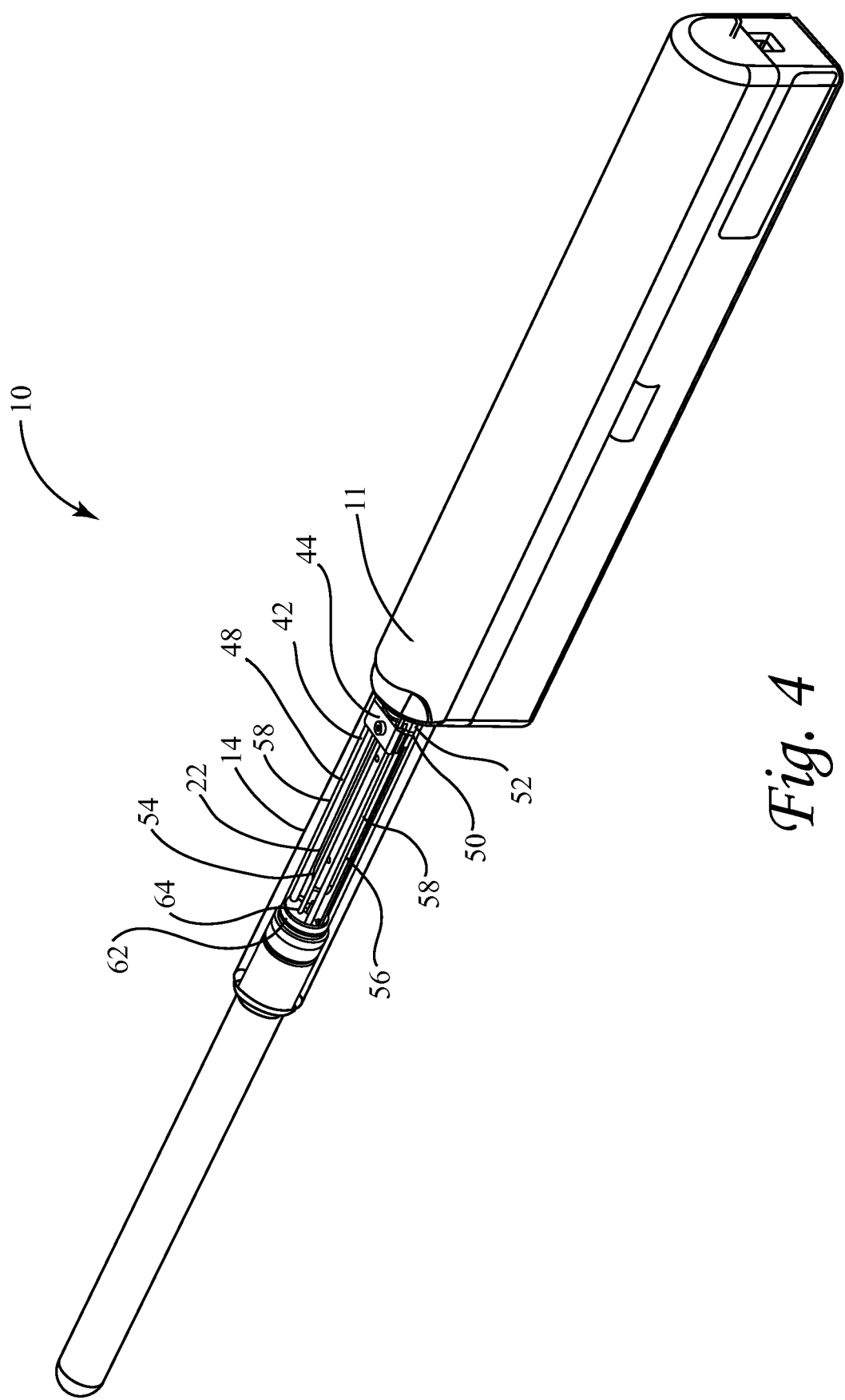

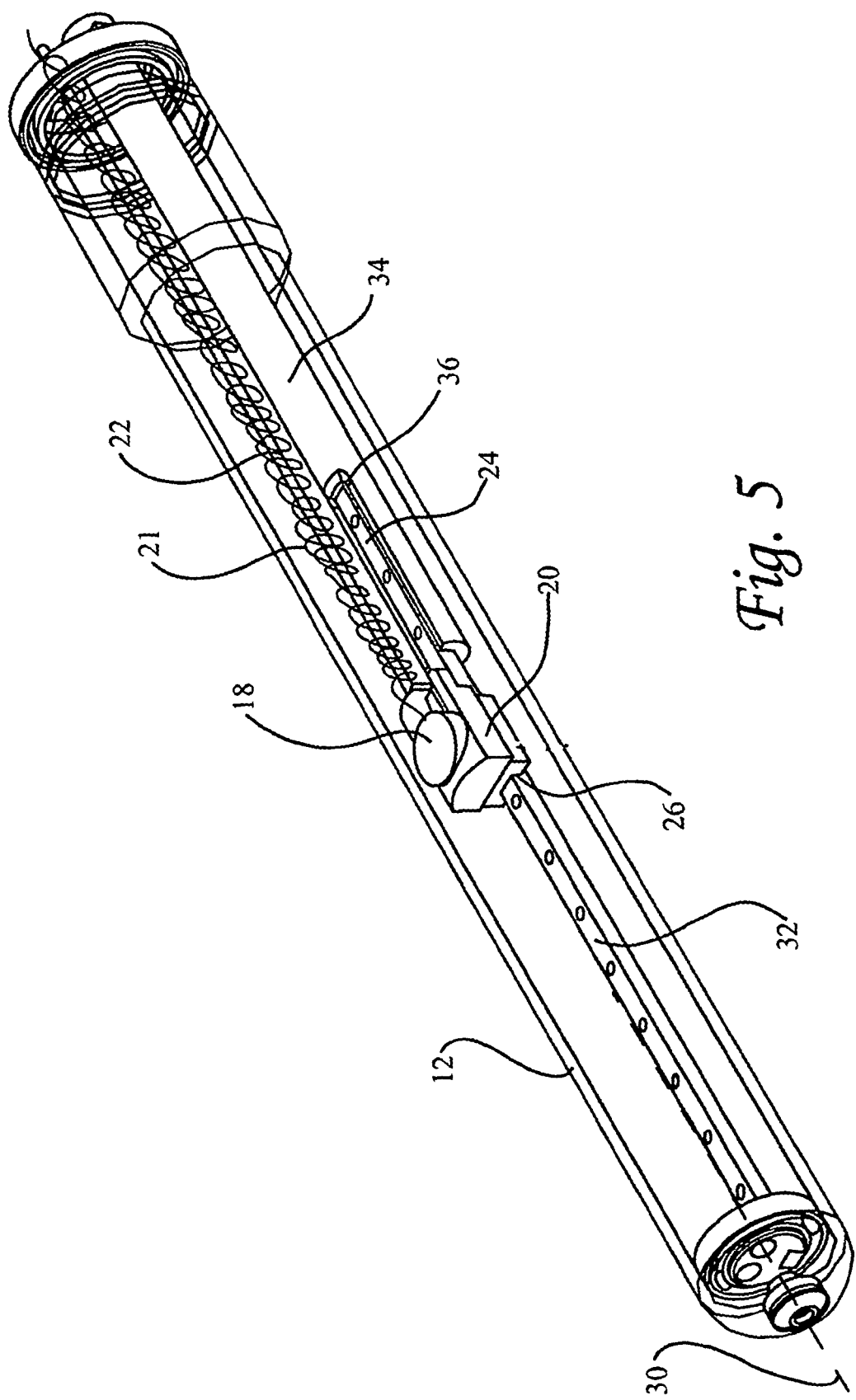

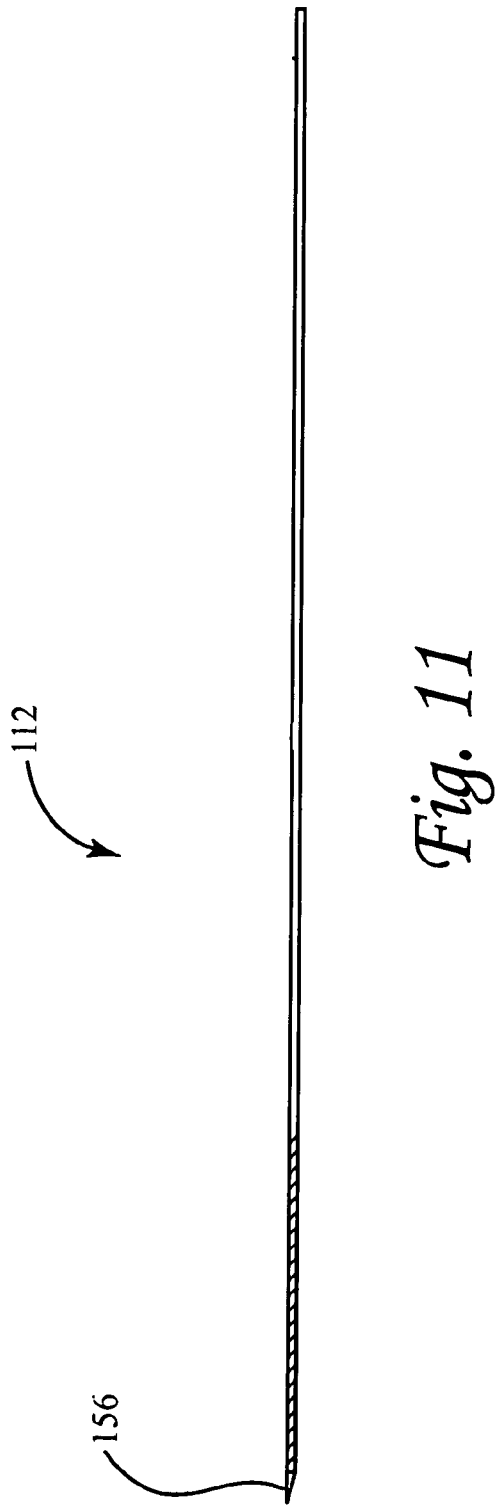

(Proir Art)

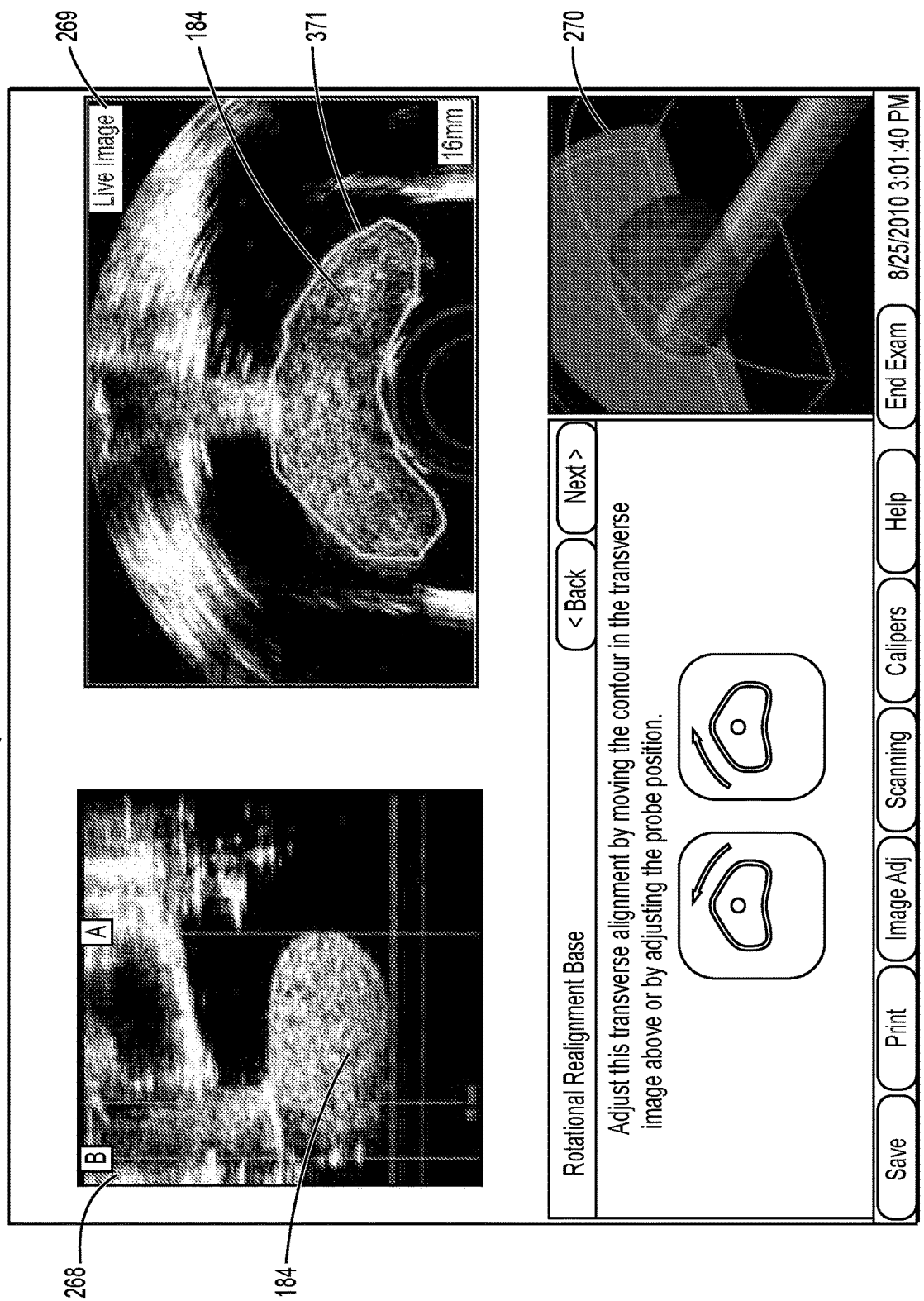

IMAGE GUIDED SURGICAL METHODOLOGY AND SYSTEM EMPLOYING PATIENT MOVEMENT DETECTION AND CORRECTION

BACKGROUND OF THE INVENTION

1. Field of the Invention

This invention relates broadly to medical imaging systems. More particularly, this invention relates to ultrasonic imaging probes and most particularly to those used in combination with flexible surgical instruments for image guided biopsy and treatment of tissue.

2. State of the Art

Ultrasound scanning is an important diagnostic tool used by medical professionals. Medical devices which employ ultrasound scanning are generally categorized as either cavital imaging devices or body imaging devices. Cavital imaging devices, often referred to as probes, are usually inserted into a cavity of the patient to take and capture images of tissue within and adjacent the cavity. Cavital probes are frequently used to provide transvaginal, transesophageal, and transrectal imaging.

Transrectal probes are important for providing guidance and assistance to an operator taking biopsy samples to test for cancers such as prostate cancer, especially in men over the age of fifty. If prostate cancer is suspected after a patient has undergone a physical examination or a Prostate Specific Antigens test, then a biopsy is typically performed to collect tissue samples from the prostate for evaluation by a pathologist. As prostate tumors are small growths which can be scattered about different portions of the prostate, multiple tissue samples (e.g., typically between 9 and 18) are usually taken from the prostate during a biopsy procedure. Performing a biopsy procedure involves inserting a transrectal ultrasonic probe into the rectum of the patient, a procedure known as a Transrectal Ultrasound (TRUS) Guided Prostate Biopsy. The probe, in conjunction with imaging software and associated equipment, generates images of two-dimensional slices of the prostate.

The adult prostate is a chestnut-shaped organ enveloped in a fibrous capsule. The base of the prostate is attached to the bladder neck, and the apex is fixed to the urogenital diaphragm. The prostate is located superiorly and posteriorly to the seminal vesicles. Anteriorly, the fibrous capsule thickens at the level of the apex to form puboprostatic ligaments which attach the prostate to the back of the symphysis pubis. Posteriorly, the two layers of Denonvilliers fascia separate the prostate from the rectum. The rectourethralis muscle attaches the rectum to the prostatic apex.

One widely-used probe for examining the prostate includes an 8-MHz transducer within an endorectal probe which can produce images in both the sagittal and axial planes. Scanning begins in the axial plane, which facilitates viewing/visualization of the base of the prostate and the seminal vesicles. A small amount of urine in the bladder facilitates this examination. First, the seminal vesicles are identified bilaterally with the ampullae of the vas on either side of the midline. The seminal vesicles are convoluted cystic structures which are darkly anechoic. The base of the prostate is then visualized. The central zone of the prostate comprises the posterior part of the gland and is often hyperechoic. The mid-portion of the prostate is the widest portion of the gland. The peripheral zone forms most of the gland's volume. Echoes are described as isoechoic and closely packed. The central part of the gland is hypoechoic and known as the transition zone. The junction of the peripheral zone and the transition zone is distinct posteriorly and characterized by a hyperechoic region which results from prostatic calculi or corpora amylacea. The transition zone is often filled with cystic spaces in patients with benign prostatic hyperplasia (BPH).

Scanning at the level of the verumontanum and observing anterior shadowing help to identify the urethra and the verumontanum. The portion of the prostate distal to the verumontanum is composed mainly of the peripheral zone. The fibrous capsule of the prostate is a hyperechoic structure that can be identified all around the prostate gland. In addition, several hypoechoic rounded structures called the prostatic venous plexi can be identified around the prostate gland. The position of the neurovascular bundles can often be identified by the vascular structures. Imaging in the sagittal plane allows for visualization of the urethra. The median lobes of the prostate are also often visualized.

Transrectal ultrasonic probes are also used to provide guidance for transperineal procedures including brachytherapy, cryotherapy or transperineal saturation biopsies. These procedures typically involve inserting needles through a grid through the perineum and utilizing the probe for guidance.

The ultrasonic probe includes one or more ultrasonic transducers which generate a narrow pulse of sound. The pulse of sound propagates through surrounding tissue and is reflected back to and captured by the transducer. The density of the tissue and its distance from the transducer affects the properties of the return signal or backscatter received by the transducer. In this manner, the properties of the return signal or backscatter can be used to construct an image of the secondary tissue.

Standard ultrasonic probes contain one or more of such ultrasonic transducers mounted inside a hollow tip. The transducer(s) pivot or quickly rotate within the tip (approximately five to ten times per second) to generate and receive pulses at multiple orientations at a given position of the probe. The probe is used to generate sagittal (or also known as longitudinal) images which are in-line with the axis of the probe and transverse images which are perpendicular to the axis of the probe tip. This dual axis image capability is referred to as bi-plane imaging. Solid-state probes utilize a plurality of very small transducers aligned in the probe (e.g., columns wrapped around a small portion of the diameter of the probe and along the length of the probe). Instead of pivoting or rotating a single transducer, the solid state probe sequentially pulses a column of the aligned transducers to create a cross sectional image of the tissue of interest. In this manner, the solid-state probe generates dual axis, bi-plane images. An example of such a probe is described in U.S. Patent Publ. No. 2007/0038112 to Taylor et al., commonly assigned to the assignee of the present application and herein incorporated by reference in its entirety.

During an ultrasonically-guided prostate biopsy procedure, once the ultrasonic probe is inserted into the rectum of the patient adjacent the prostate, images generated by the probe are used to identify the particular portion(s) of the prostate to biopsy, and to properly position the probe, a guide assembly coupled to the probe, and a needle assembly which is subsequently advanced through the guide assembly. The guide assembly guides the distal end of the needle assembly through the rectal wall to a fixed position and orientation adjacent the prostate. Additional images generated by the probe during the procedure help the physician to monitor and verify the depth and position of the needle assembly within the prostate.

The needle assembly typically includes a wire shaped biopsy needle and an outer cylindrically-shaped cannula which receives and supports the biopsy needle. The needle assembly is often coupled to and operably disposed within a spring loaded instrument, typically referred to as a biopsy gun. The biopsy gun is used to advance the needle of the needle assembly into the prostate. During a first firing of the biopsy gun, the needle rapidly advances relative to the cannula into the prostate over a distance called the stroke length, which is typically between 15 mm to 25 mm. A second firing of the biopsy gun causes the cannula to advance over the exposed notch portion of the needle in the prostate. As the cannula advances over the exposed notch portion of the needle, it cuts and severs tissue surrounding the needle and traps the tissue within the notch portion, thus capturing a tissue sample. The needle and cannula are then withdrawn from the patient with the tissue sample captured within the cannula. This process can be repeated at multiple tissue locations in the prostate. An example of such a system is described in U.S. Patent Publ. No. 2005/0159676 to Taylor et al., commonly assigned to the assignee of the present application and herein incorporated by reference in its entirety.

Controlled movement of a transducer over a range of locations within a probe allows for more accurate and complete imaging, and requires less movement or positioning of the probe. U.S. Pat. No. 5,592,942 to Webler et al. discloses an automated longitudinal position translator for ultrasonic imaging probes, and methods of using such probes within a blood vessel. U.S. Pat. No. 6,004,271 to Moore discloses a combined motor drive and automated longitudinal position translator for an ultrasonic imaging system. U.S. Pat. No. 6,200,269 to Lin, et al. discloses a forward scanning ultrasound catheter probe which maintains a transducer on a platform at a distal end of the probe and pivots the platform via a piezoelectric drive to create a scanning plane. Controlled translational and rotational movement of a transducer in a transrectal probe is disclosed in U.S. Patent Publ. No. 2007/0038112 to Taylor et al., commonly assigned to the assignee of the present application and incorporated by reference above in its entirety.

SUMMARY OF THE INVENTION

The invention is directed to a methodology (and system based thereon) that utilizes a biopsy needle guide assembly mounted on an ultrasonic scanning probe for image-guided biopsy sampling of target tissue such as a prostate. The methodology and corresponding system can be utilized with a biopsy needle guide assembly and ultrasonic scanning probe as described in U.S. Patent Publ. No. 2007/0038112 and U.S. Patent Publ. No. 2005/0159676, which are incorporated by reference above in their entireties. The methodology and corresponding system can also be utilized with a biopsy needle guide assembly and ultrasonic scanning probe as described in U.S. patent application Ser. No. 12/834,357, entitled "Biopsy Needle Assembly" and U.S. patent application Ser. No. 12/834,384, entitled "Scanning Probe", which are commonly assigned to the assignee of the present application and herein incorporated by reference in their entireties.

The ultrasonic scanning probe provides for controlled translational and rotational movement of an ultrasonic transducer inside and across a substantially narrow distal scanning portion of the probe's housing. The narrow distal scanning portion of the probe's housing facilitates positioning and orienting the probe at different angles within the patient about the prostate, and imaging and biopsying the prostate.

The biopsy needle guide assembly is moveably mounted on the exterior of the probe's housing and provides at least one guide channel that extends between an inlet and an outlet. The inlet receives the distal end of a biopsy needle assembly. The guide channel functions to bend and guide the needle assembly as the needle assembly is advanced therethrough such that the distal end of the needle assembly exits the outlet of the guide channel at a predetermined orientation and direction. The needle guide assembly can be moved relative to the probe through various rotational angles and translational distances relative to the probe to position the guide assembly at various locations and orientations relative to the target tissue. In this manner, the needle assembly is directed by the guide assembly in a predetermined controlled direction to facilitate placement of the needle assembly into the desired tissue to be sampled.

The biopsy needle assembly includes a flexible biopsy needle and an outer cannula for receiving and supporting the biopsy needle. The needle has a tissue piercing distal end and a sampling section proximal to the tissue piercing distal end. The cannula defines a flexible hollow elongate body with a tissue piercing distal tip. The elongate body of the cannula defines a lumen which extends through the elongate body. The biopsy needle is insertable into and longitudinally translatable through the lumen of the cannula. The biopsy needle guide assembly is mounted within a hand-holdable biopsy gun that imparts controlled movement to the needle and cannula of the needle assembly under user-control to carry out tissue sampling as described herein.

The probe is operably coupled to a data processing system (e.g., a PC computer with standard display software) which displays images of the target tissue scanned by the probe for image-guided biopsy sampling of target tissue.

During an image-guided biopsy of the prostate, the probe is inserted into the rectum of the patient adjacent the prostate and held by a cradle in a fixed stationary position. The rotational orientation and longitudinal position of the needle guide assembly relative to the probe can be adjusted as desired. The probe is operated to capture two dimensional images of the prostate. The images are displayed by the data processing system to provide visual guidance in planning the biopsy procedure, and preferably to provide visual feedback as to the positioning and depth of the guide assembly in carrying out the planned biopsy procedure while monitoring and adjusting for patient movement. Once the probe and needle guide assembly are properly positioned, the distal end of the needle assembly is advanced manually through the guide channel of the needle guide assembly until it is in a desired position extending from the outlet of the guide channel. The guide channel dictates the direction and orientation of the needle assembly as it exits the guide channel. The biopsy gun is then operated by a sequence of two firings to advance the needle assembly into the prostate of the patient for sampling the tissue of the prostate. During a first firing, the biopsy gun rapidly moves the sampling portion of the needle out of the cannula and into the desired sample section of the prostate. During a second firing, the biopsy gun moves the outer cannula over the exposed sampling section of the needle, which traps sample tissue within sampling section of the needle between the cannula and the needle sampling section. The needle assembly is then withdrawn from the patient with the tissue sample trapped within the cannula. The guide assembly is then adjusted to a new position and/or orientation on the probe as desired, and the process is repeated as needed.

The data processing system of the present invention employs software logic that facilitates image-guided biopsies of target tissue while monitoring for patient movement during the biopsy procedure. During operation, the software logic interacts with an operator (e.g., a physician) to create/define a biopsy plan which includes a specified number of sample needle paths. The needle paths are the paths (e.g., a direction and a distance) through which the needle assemblies will be advanced to procure the desired biopsy samples of the prostate. The needle paths are preferably derived by the data processing system according to pre-defined templates. Such pre-defined templates can target areas of the prostate where cancer is most likely to be found. The system calculates the biopsy plan based on the size of the prostate and the particular biopsy pattern selected (e.g., number of samples and desired distribution of the samples). The system is also optionally configurable to allow the operator to create, add and/or remove needle paths to/from a selected biopsy plan. These decisions may be based on knowledge gleaned from prior scans and procedures and/or from current images of the prostate.

Initially, the system interacts with the operator to input (e.g., mark) spatial attributes of various features of the prostate in predetermined image planes (e.g., the center sagittal image plane and the transverse imaging plane where the profile of the prostate is the "widest") displayed on a display device. The 'center sagittal image plane' used herein refers to the sagittal image plane which passes through the approximate center of the prostate and thus divides the prostate into two halves. The operator-inputted spatial attribute(s) can be input by touch screen input, a pointing device such as a mouse or trackball, or other suitable input device. This interactive process is referred to herein as operator-assisted feature localization. The features of the prostate (along with the operator-inputted spatial attribute(s) of the features of the prostate) preferably correspond to the boundary of the prostate. For example, the features of the prostate can be selected from a group including the base, the apex, the anterior edge, the posterior edge, the right angular boundary, the left angular boundary, and a contour line that surrounds the prostate. The operator-inputted spatial attribute(s) of the features of the prostate are used by the system to automatically derive the volume of the prostate and/or perform a full three dimensional scan of the prostate. The full three dimensional scan of the prostate is carried out over a series of scan planes that are distributed over the three-dimensional volume of the prostate. The scan planes can include sagittal scan planes sampled at a regular angular spacing and/or transverse scan planes sampled at a regular depth spacing. If only one of these two sets of data is taken or available, then one may be interpolated from the other. The system's software logic maintains an image buffer for storing the two dimensional image data derived from sagittal and/or transverse scan planes of the prostate.

Upon completion of the full three dimensional scan of the prostate, the system interacts with the operator to select one of a number of predefined biopsy patterns. The patterns vary in terms of total number of samples (e.g., between nine and eighteen) and the distribution of the samples through the prostate. Upon such operator selection (or possibly in advance of such operator selection), the system automatically derives a set of needle paths (i.e., a direction and distance) that correspond to the sample locations of the operator-selected biopsy pattern, as well as the coordinates at which the guide assembly will need to be positioned for each needle path. The system can display one or more three dimensional images of the prostate together with graphical representations of the needle paths for visualization of the biopsy plan. The system can also be configured to interact with the operator to accept, add, remove and/or customize the needle paths of the biopsy plan.

Once the biopsy plan is completed and confirmed, the system interacts with the operator to initiate the procurement of biopsy samples of the prostate in accordance with the biopsy plan. In the preferred embodiment, the sequence in which the biopsy samples are taken is generally from the base of the prostate to the apex of the prostate. For each given needle path in the biopsy plan, the system interacts with the operator to facilitate guided placement and positioning of the needle guide assembly (via manual or automated adjustment) in a longitudinal position and rotational orientation which will direct a needle assembly along the given needle path. For example, the system can output specific mechanical adjustment settings (e.g., a longitudinal coordinate and a rotational coordinate) for positioning the needle guide assembly in the longitudinal position and rotational orientation corresponding to the given needle path. After moving the guide assembly into position for a given needle path, the operator operates the biopsy gun to carry out a sequence of two firings which advance the needle assembly through the guide assembly and along the given needle path to procure a first biopsy sample from the prostate. Additional ultrasound image(s) may be taken and saved on the hard disk or other data storage device to create a permanent record of the biopsy tissue location. The operator removes the needle assembly containing the captured tissue sample, removes the captured tissue sample from the needle assembly, and places it into a tissue specimen dish. This procedure is repeated for each needle path of the biopsy plan.

In accordance with the invention, the data processing system enables the operator to visually detect patient movement during the procurement of biopsy samples of the prostate in accordance with the biopsy plan. More specifically, prior to acquiring a particular sample, the system controls the probe to rescan a predetermined image plane (preferably the center sagittal image plane) which was previously scanned and displayed by the system in conjunction with the prior operator-assisted feature localization. The system displays the refreshed image data of the predetermined image plane (as captured by the rescanning of the probe) in a predefined display window, and superimposes onto the image displayed in the display window a graphical representation (e.g., a vertical or horizontal line, an icon or other display element) for one or more features (e.g., the base and apex of the prostate) identified in the prior operator-assisted feature localization process. The graphical representation for a given feature is displayed at a display window location corresponding to the operator-inputted marked spatial attribute(s) of the given feature as defined in the prior operator-assisted feature localization process. In this manner, the predefined display window allows the operator to visually compare the current spatial attribute(s) of one or more features of the prostate with the operator-inputted spatial attribute(s) of the one or more features as defined in the prior operator-assisted feature localization process. If the operator visually observes misalignment between the image data displayed in the predefined window and the graphical representation(s) overlaid thereon (e.g., a shift in the spatial attributes of one or more features), then such results indicate that the patient has moved relative to the probe and needle guide assembly. The probe and needle guide assembly may then be re-positioned in order to correct for such patient movement. If there is no patient movement (or the probe and needle guide assembly have been re-positioned to correct for any patient movement), the operator can then continue with the procedure to acquire the particular sample. The visual interaction with the operator that allows for operator-assisted detection of patient movement is preferably carried out prior to positioning the needle guide assembly for acquisition if the particular sample. It can also be carried out after positioning the needle guide assembly or at some other time prior to acquisition of the sample in accordance with the biopsy plan.

The methodology and system of the invention can utilize ultrasonic imaging to provide guidance during the procedure. The methodology and system of the invention can utilize other suitable medical imaging techniques to provide guidance during the procedure.

The methodology and system of the present invention may also be used to visually detect patient movement during image-guided transrectal treatment procedures including brachytherapy, cryotherapy or other transrectal procedures in which a flexible instrument is guided by the guide assembly of the system to apply treatment to or otherwise act on a localized target site of the prostate.

The methodology and system of the invention may also be used to visually detect patient movement during image-guided transperineal treatment procedures including brachytherapy, cryotherapy or other transperineal saturation biopsies in which the needle assembly is inserted through a grid through the perineum and transrectal images from the probe are used for guidance.

The methodology and system of the invention may also be used to visually detect patient movement during image-guided laparoscopic and non-laparoscopic surgeries involving other cavities and tissues such as the abdominal cavity (e.g., surgeries involving the small intestine, large intestine, stomach, spleen, liver, pancreas, kidneys, and adrenal glands), the thoracic cavity, and the pelvic cavity.

Additional objects and advantages of the invention will become apparent to those skilled in the art upon reference to the detailed description taken in conjunction with the provided figures.

BRIEF DESCRIPTION OF THE DRAWINGS

FIG. 3 is a perspective view of the probe of FIG. 1 with a first elongate portion of the housing shown transparent.

FIG. 4 is a perspective view of the probe of FIG. 1 with a second elongate portion of the housing shown transparent.

FIG. 5 is an enlarged view of the connectors, sled, and transducer of FIGS. 3 and 4.

FIG. 11 is a side view of the cannula.

FIG. 19B is a graphical user interface for repositioning the rotational position of the probe and the needle guide assembly (or an operator-inputted spatial attribute of a feature of the prostate) in order to correct for rotational movement of the patient relative to the probe.

DETAILED DESCRIPTION OF THE PREFERRED EMBODIMENTS

Figure 1:
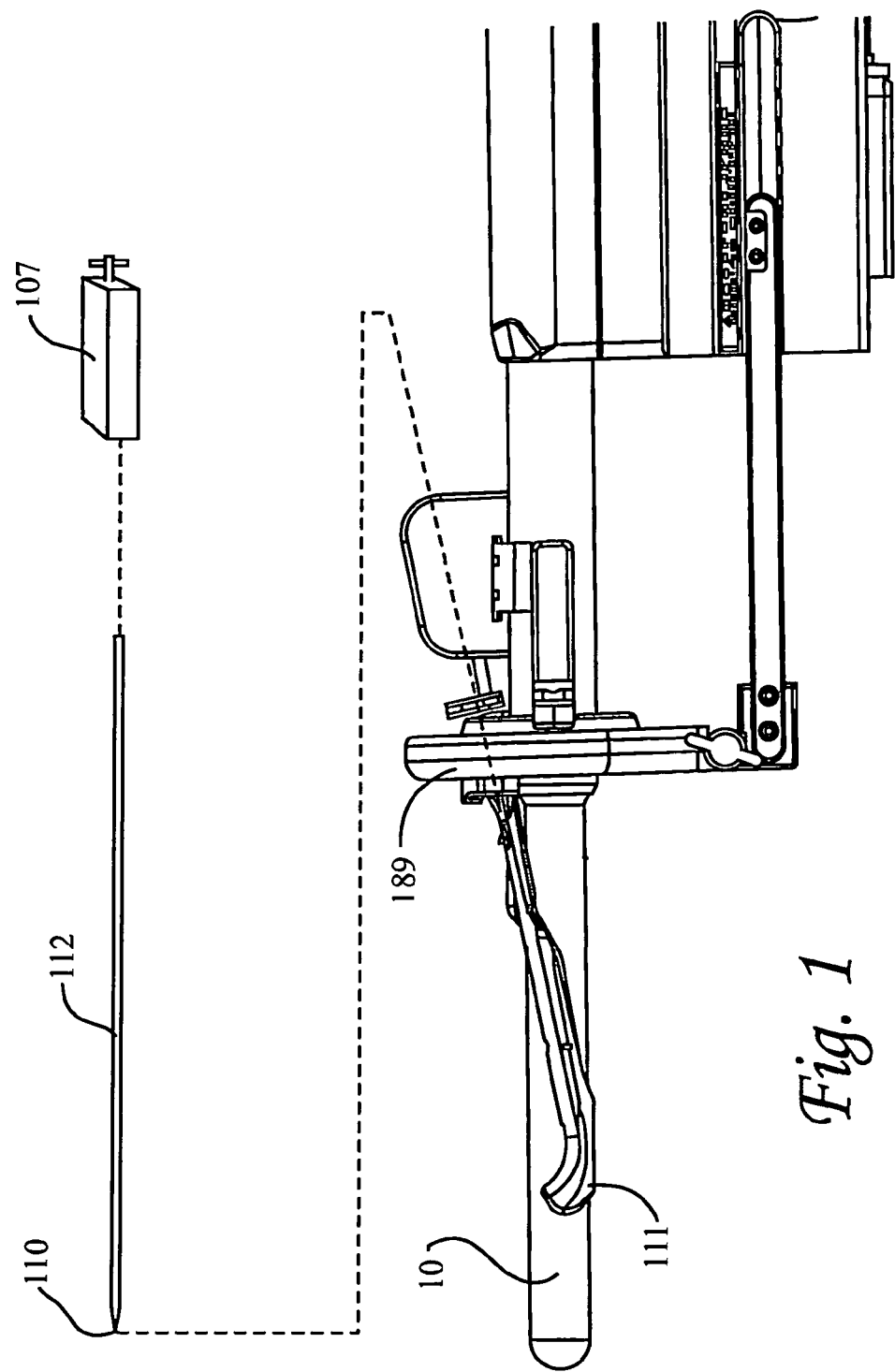
FIG. 1 is a partially exploded view of the preferred embodiment of the probe and needle assembly delivery system used in conjunction with the data processing system and method of the invention.

Turning now to FIG. 1, an improved transrectal ultrasonic probe 10 is shown in conjunction with a biopsy needle 110, a cannula 112 for receiving and supporting the biopsy needle 110, and a delivery system which includes a guide assembly 111 for guiding the biopsy needle 110. The needle 110 and cannula 112 are preferably at least partially disposed within and coupled to a biopsy gun 107. The biopsy needle 110, cannula 112, guide assembly 111, and biopsy gun 107 are further discussed below with respect to the operation of these devices in conjunction with the improved probe 10 to capture biopsy tissue samples in a patient.

Figure 2:
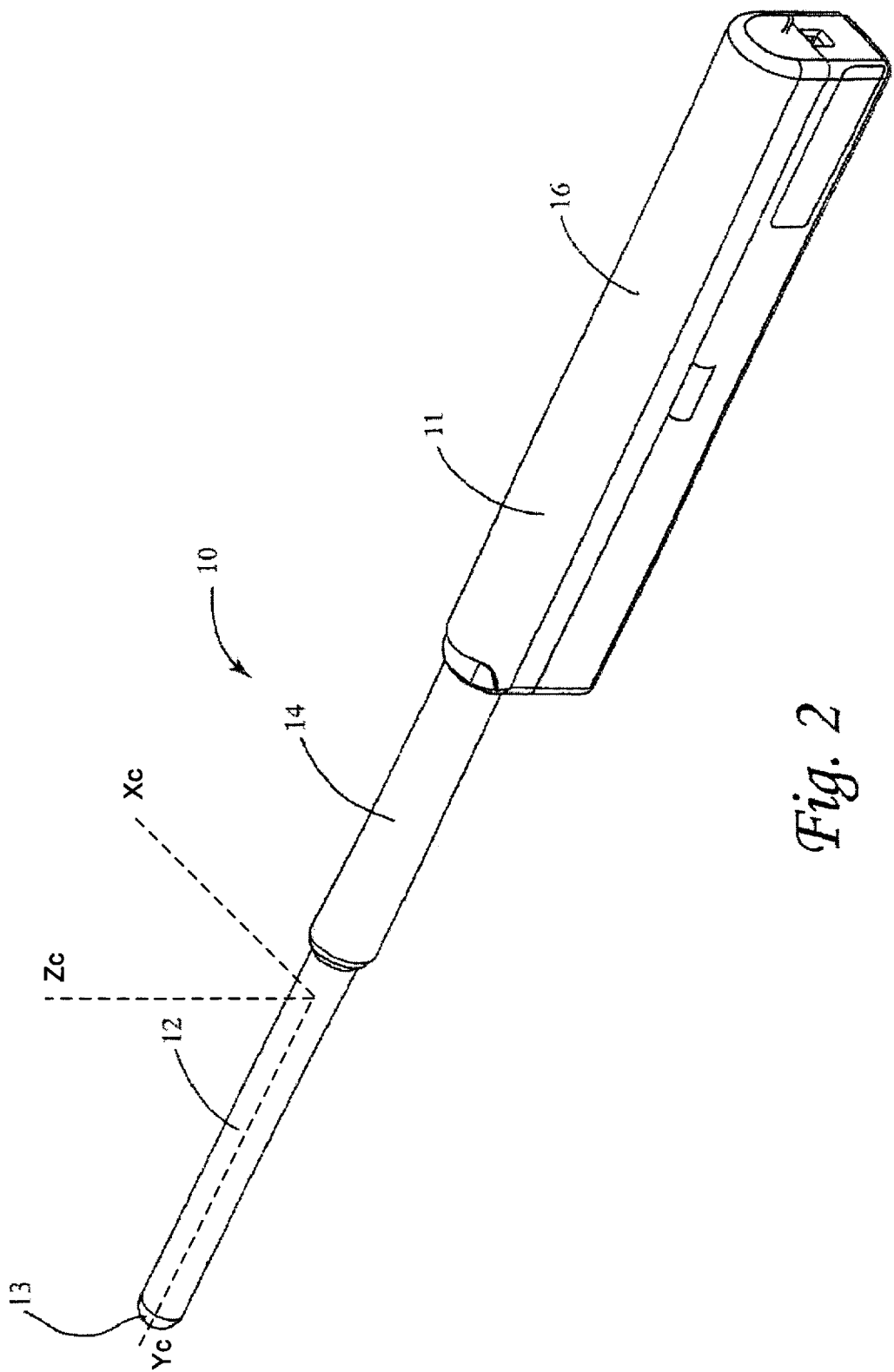
FIG. 2 is a perspective view of the probe of FIG. 1.

The improved probe 10 is best seen with reference to FIGS. 2-7. Turning to FIG. 2, the probe 10 has a housing 11 which includes a first elongate portion 12, a second elongate portion 14 proximal of the first elongate portion, and a third elongate portion 16 proximal of the second elongate portion 14. The first elongate portion 12 is substantially narrower (e.g., has a substantially smaller cross sectional area) than the second elongate portion 14, and preferably has a circular cross section with an outside diameter of approximately 0.745 inches, preferably between 0.740 inches and 0.750 inches. The second elongate portion 14 preferably has a circular cross section with an outside diameter of approximately 1.06 inches, preferably between 0.75 inches and 1.4 inches. The third elongate portion 16 preferably has an outer body width of approximately 1.62 inches, preferably between 1.4 inches and 2.0 inches. The probe 10 also includes a distal end 13 which is preferably spherically shaped with a decreasing cross sectional area in the distal direction to assist with insertion of the probe 10 into a patient. During use, the first elongate portion 12 is inserted into the rectum of the patient with the larger second elongate portion 14 remaining outside of the rectum of the patient.

Turning to FIGS. 3 and 5, the first elongate portion 12 of the housing 11 houses an ultrasonic transducer 18 which is capable of emitting acoustic energy through the first elongate portion 12 and surrounding body cavity and tissue, and detecting acoustic backscatter signals. The transducer 18 is preferably mounted on a sled 20 which is rigidly coupled to a first connector 22 and slidably coupled to a guide portion 32 of a second connector 24 via a slot 26 defined by the bottom portion of the sled 20. In this configuration, the transducer 18 is longitudinally translatable through the first elongate portion 12, preferably parallel to a central axis 30 extending through the first elongate portion 12.

The first connector 22 translates longitudinally through the first elongate portion 12, and functions to push and pull the transducer 18 distally and proximally along the guide portion 32 of the second connector 24. A coiled coax 21 which carries transducer signal data is preferably wrapped around the first connector 22 as shown. The second connector 24 includes both the guide portion 32 and a support brace 34. The guide portion 32 is preferably made from metal or steel and is rigidly attached to the distal end 13 of the probe 10. The guide portion 32 preferably extends parallel to the central axis 30. The support brace 34 defines a slot 36 (FIGS. 5, 6) for receiving a proximal section of the guide portion 32 and functions to support the guide portion 32. The support brace 34 is made of a plastic material that allows it to deflect to prevent binding thereof when the first elongate portion 12 of the probe 10 is bent. The second connector 24 thus provides a guided pathway for directing longitudinal translation of the sled 20 as well as the transducer 18. The second connector 24 minimizes unwanted movement of the sled 20 and transducer 18. The second connector 24 rigidly maintains the radial position of the sled 20 and transducer 18 relative to the first elongate portion 12 of the housing 11 and provides support to the sled 20 and transducer 18. The first and second connectors 22, 24 extend between the first and second elongate portions 12, 14 of the housing 11, and respectively attach to a movable member and a platform assembly within the second elongate portion 14 as further discussed below with respect to FIGS. 4 and 6.

Figure 6A:
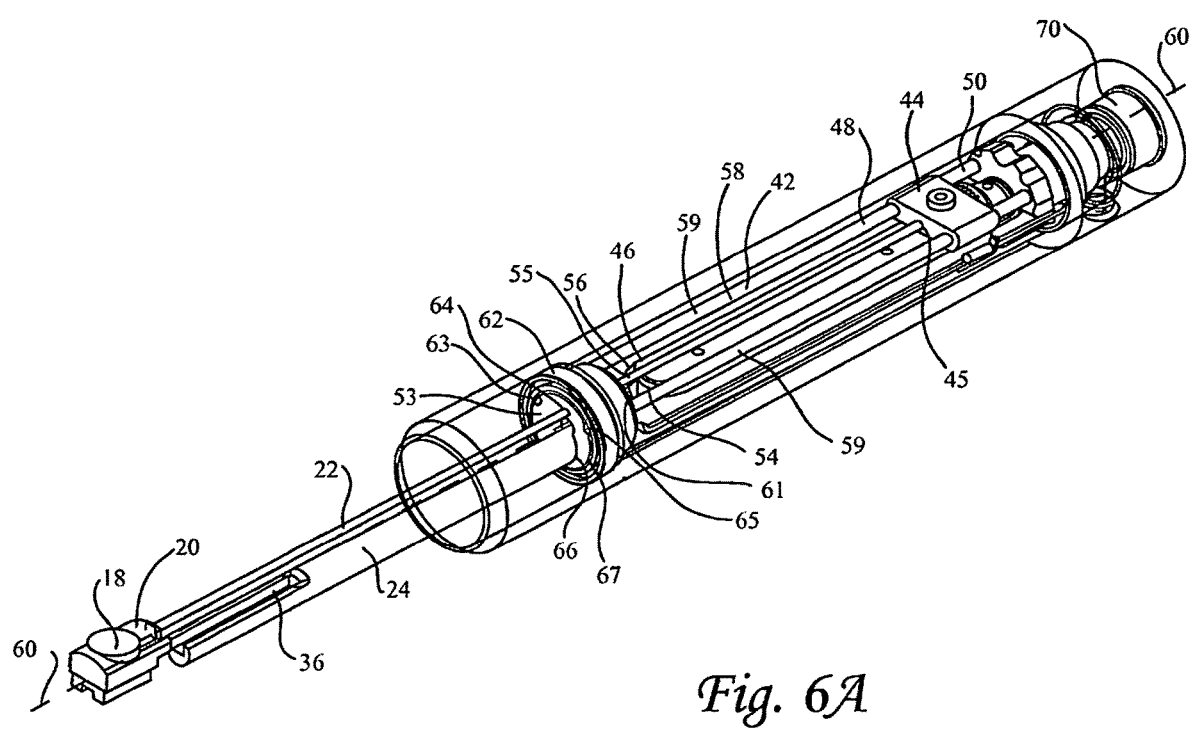
FIG. 6A is an enlarged view of the platform assembly, movable member, connectors, transducer, and sled of FIGS. 3 and 4 without the guide section of the second connector.
Figure 6B:
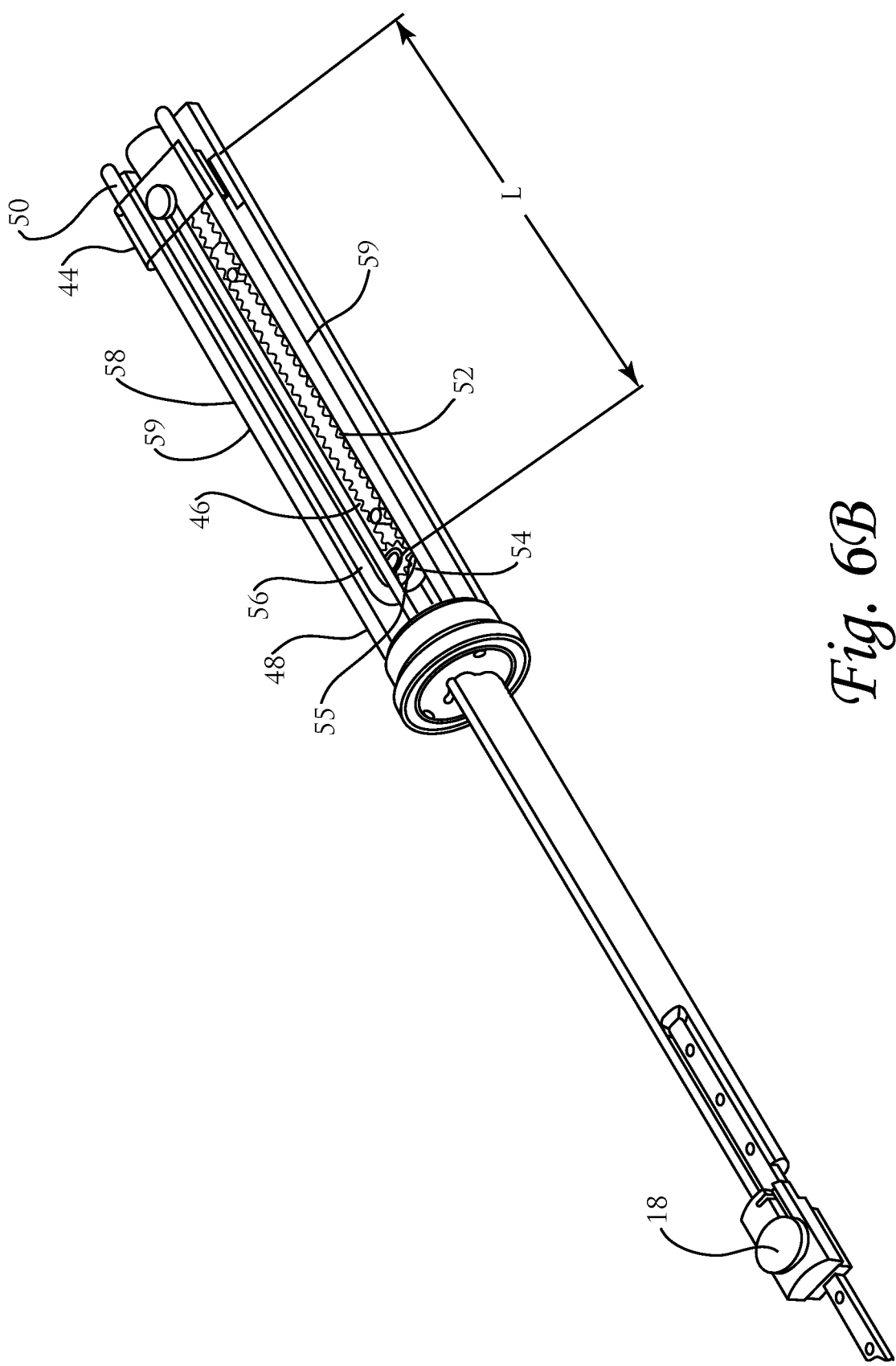
FIG. 6B is an enlarged alternate view of the platform assembly, movable member, connectors, transducer, and sled of FIG. 6A.

Turning now to FIGS. 4, 6A, and 6B, the second elongate portion 14 of the housing 11 houses a platform assembly 42 which is rotatable within and relative to the second elongate portion 14 and longitudinally fixed relative thereto. The platform assembly 42 supports a movable member 44 which translates relative to a frame 48 of the platform assembly 42. The movable member 44 is both rotatable within and relative to the second elongate portion 14, and translatable therethrough. The platform assembly 42, in addition to the frame 48, includes a transmission system 46. The transmission system 46 functions to drive reciprocating proximal and distal translation of the movable member 44 through the second elongate portion 14, and preferably converts rotation of a proximally situated drive shaft (further discussed below) into the translation of the movable member.

In the preferred embodiment, the transmission system 46, best seen in FIG. 6B, includes a vertical bevel gear 50, a horizontal bevel gear 52, a belt pulley 54, a belt 56, and an integral belt pin (not shown). The horizontal bevel gear 52 engages with the vertical bevel gear 50, and the belt 56 and belt pulley 54 rotate with the horizontal bevel gear 52. The integral belt pin is fixed to the belt 56, and is positioned in and slidable through a slot (not shown) on a bottom side of the movable member 44. As the belt pulley 54 rotates, the pin moves with the belt 56 and pulls the movable member 44 along with it. When the pin reaches and traverses one of the proximal (hidden) and distal 55 arced ends of the belt pulley 54, it slides through the slot in the bottom of the movable member 44 and then pulls the movable member 44 in the opposite direction as it circles back with the belt 56 toward the other of the proximal and distal 55 arced ends of the belt pulley 54.

In the preferred embodiment, the frame 48 of the transmission system 46 (best seen in FIG. 6A) includes at least one track 58 which supports the movable member 44 and preferably extends parallel to a linear axis 60 through the second elongate portion 14. The at least one track 58 may include, for example, two parallel beams or rails 59. The movable member 44 is preferably a sled which is slidably coupled to the track 58 of the frame 48 as shown. The frame 48 includes a neck 61 that interfaces to a bearing 62. The bearing 62 includes an outer race which is longitudinally and rotatably fixed relative to the second elongate portion 14 of the housing 11, and an inner race 67 which is rotatable relative to the outer race and second elongate portion 14. The neck 61 includes a plate portion 53 which is preferably situated in an interference fit with the inner race 67 of the bearing 62. The plate portion 53 defines a first hole 64 for slidably receiving the first connector 22, and a second hole 66 for rigidly receiving the second connector 24. The bearing 62 functions to provide support to the frame 48 and first and second connectors 22, 24, and to prevent radial movement thereof relative to the housing 11. The plate portion 53 includes additional holes 63, 65 for allowing the ultrasonic fluid to freely flow between the first and second elongate portions 12, 14. The proximal end of the second elongate portion 14 is sealed so that no fluid flows into the third elongate portion 16. The first connector 22 extends through the hole 64, preferably parallel to the linear axis 60 between the parallel rails 58 of the frame 48, and is rigidly coupled the movable member 44 at a proximal end 45. The second connector 24 extends through the hole 66, preferably parallel to the linear axis 60, and is rigidly coupled to the neck 61 of the frame 48.

Based on the above arrangement, it will be appreciated that continued rotation of the vertical bevel gear 50, horizontal bevel gear 52, and belt 56 of the transmission system 46 causes reciprocating proximal and distal longitudinal translation of the movable member 44 along a characteristic length L of the track 58 of the frame 48.

It will also be appreciated that the first connector 22 rigidly couples the transducer 18 in the first elongate portion 12 of the housing 11 to the movable member 44 in the second elongate portion 14 of the housing 11, and thus that reciprocating proximal and distal longitudinal translation of the movable member 44 along the characteristic length L caused by the transmission system 46 causes reciprocating proximal and distal longitudinal translation of the transducer 18 within the first elongate portion 12 of the housing 11 along a length equivalent to the length L. The first connector 22 thus has a length which preferably exceeds the characteristic length L, and also which preferably exceeds the longitudinal length of the second elongate portion 14 such that when the movable member 44 is disposed in the proximal-most position in the frame 48 (e.g., FIGS. 4 & 6B), the first connector 22 still extends through the entire second elongate portion 14 and into the first elongate portion. The second connector 24 also preferably has a length which exceeds the characteristic length L as well as the longitudinal length of the second elongate portion. The second connector 24 slidably couples the transducer 18 to the platform assembly 42. Thus, rotation of the entire platform assembly 42 about the central axis thereof 60 in either a clockwise or counterclockwise direction relative to the second elongate portion 14 of the housing 11 drives rotation of the movable member 44 and first and second elongate members 22, 24, which causes the transducer 18 to rotate in the same direction within the first elongate portion 12 about the central axis 60.

As alluded to above, the first and second elongate portions 12, 14 of the housing 11 are fluidly coupled with each other and filled with an ultrasonic coupling medium (e.g., ultrasonic transmission oil) which flows freely between the first and second elongate portions 12, 14. It will be appreciated that movement of the transducer 18, sled 20, movable member 44, connector(s) 22, 24, and platform assembly 42 within the housing 11 will cause zero net displacement of the ultrasound coupling medium, which eliminates changes in pressure in the fixed volume of the first and second elongate portions 12, 14 of the probe and allows rotatable seals disposed on a drive shaft (further discussed below) to maintain the oil within the first and second elongate portions 12, 14 and prevent air from entering therein. If the net displacement of the ultrasound coupling medium within the first and second elongate portions were to change, then the rotatable seals could fail, causing leakage to occur and potentially causing deterioration of the quality of the image generated from the probe 10.

Figure 7:
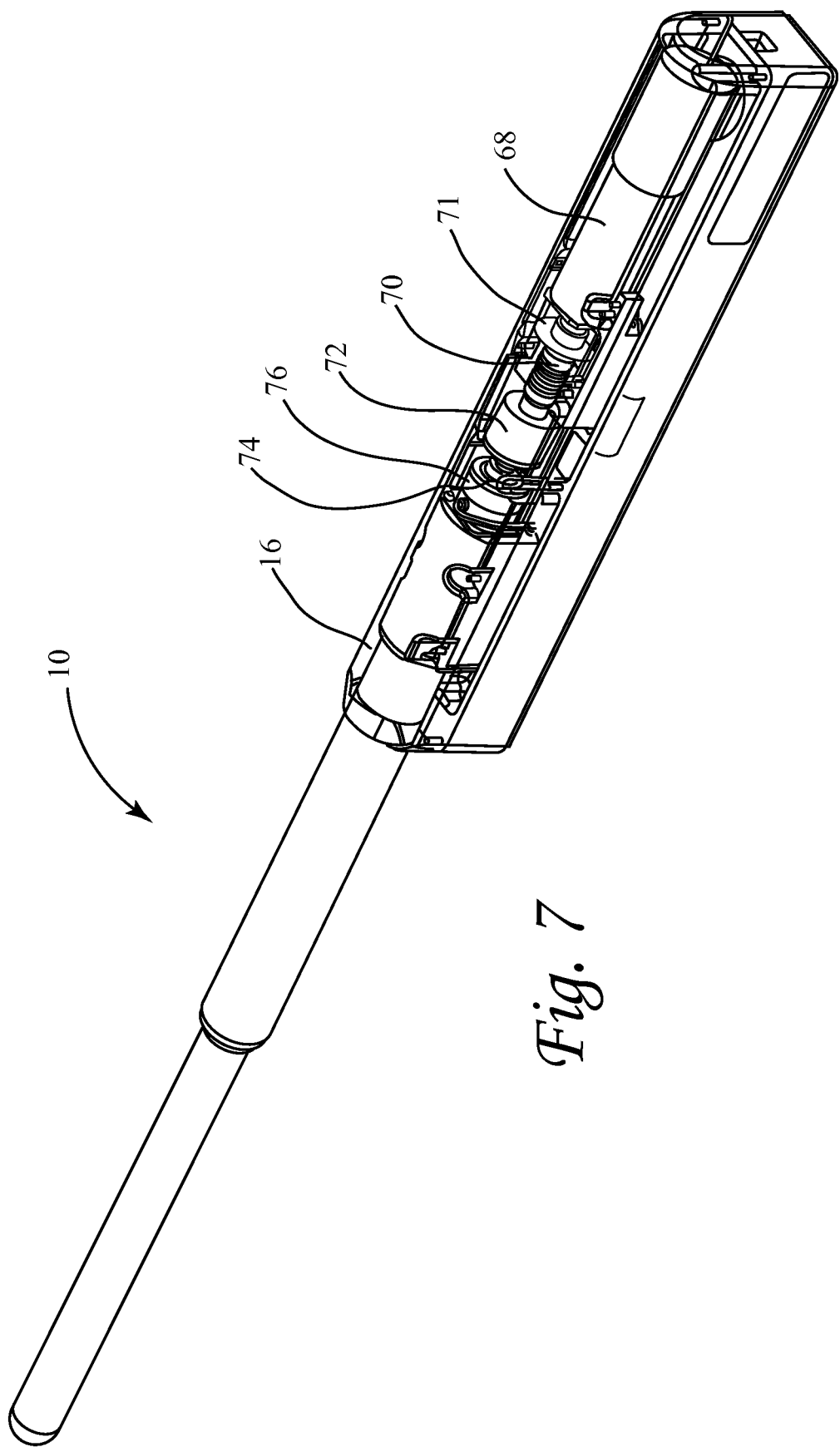
FIG. 7 is a perspective view of the probe of FIG. 1 with a third elongate portion of the housing shown transparent.

Turning to FIG. 7, the third elongate portion 16 of the housing 11 can function as a handle for manual operation of the probe 10, or can be grasped by a stand for automated operation thereof. In the preferred embodiment, the third elongate portion 16 houses a motor, clutch, brake, and control circuitry for driving the rotation of two coaxial drive shafts coupled to the frame 48 and the transmission system 46 of the platform assembly 42 in order to selectively rotate and translate the transducer 18 as further discussed below. As shown, the third elongate portion 16 preferably houses a single motor 68 which rotatably drives an inner drive shaft 70. The inner drive shaft 70 extends from the motor 68 through the third elongate portion 16 of the housing 11 to the proximal end of the second elongate portion 14 where it is rotatably coupled to the vertical bevel gear 50 of the transmission system 46 (FIGS. 6A, 6B). The inner shaft 70 thus linearly and reciprocally drives the movable member 44. An electrically controlled clutch 72 is mounted about the inner shaft 70 within the third elongate portion 16, and an outer shaft 74 extends from the clutch 72. The outer shaft 74 is hollow and surrounds the inner shaft 70, which extends through it. The outer shaft 74 extends from the clutch 72 through the third elongate portion 16 of the housing 11 to the proximal end of the second elongate portion 14 where it is rotatably fixed to the frame 48 of the platform assembly 42. An electrically controlled brake 76 is mounted about the outer shaft 74 within the third elongate portion 16 forward of the clutch 72, and is operable to prevent rotation of the outer shaft 74.

The clutch 72 and brake 76 operate under control of electrical signals supplied by a motor control processor unit (MCPU). The MCPU can issue a signal which engages or disengages the clutch 72 and brake 76. When the clutch 72 is engaged, it locks (rotatably fixes) the inner and outer shafts 70, 74 to each other such that the outer shaft 74 is rotated by the rotation of the inner shaft 70. As the outer shaft 74 is rotatably fixed to the frame 48 of the platform assembly 42, when the clutch 72 is engaged and the brake is disengaged, rotation of the inner shaft 70 by the motor 68 drives rotation of the outer shaft 74 and the entire platform assembly 42 about its central axis 30 without operating the transmission system 46. When the clutch 72 is unengaged and the brake is engaged, rotation of the inner shaft 70 by the motor 68 operates the transmission system 46 as the inner shaft 70 rotates relative to the outer shaft 74.

The probe 10 preferably includes an outer shaft encoder (not shown) and an inner shaft encoder 71 for monitoring the longitudinal and rotational position of the transducer 18. The encoders each include a wheel which rotates with a respective shaft, and a sensor which monitors the rotational position of the wheel as known in the art. The encoders send signals to the MCPU 73 indicative of the longitudinally and rotational position of the transducer 18. Such rotational and positional feedback allows for accurate positioning and rotation of the transducer 18 within the probe 10.

Figure 8:
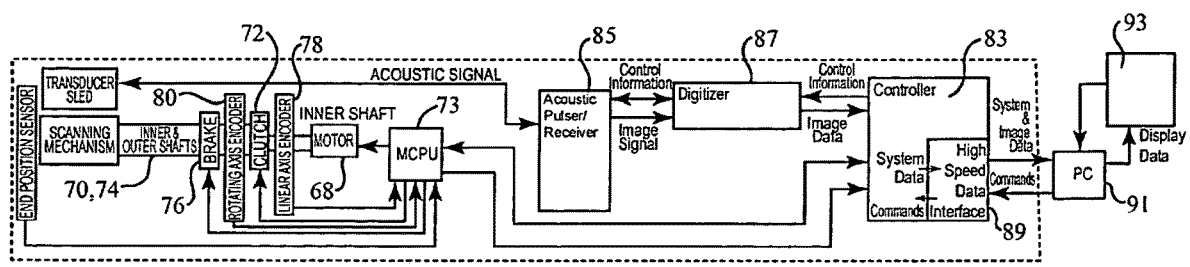
FIG. 8 is a block diagram of the single motor scanning probe and circuit board of the integrated electronics of the probe assembly.

Turning to FIG. 8, the clutch 72 and brake 76 are controlled by a motion control processing unit (MCPU) 73. The MCPU 73 is operatively connected to a control box or PC. In response to operation command signals received from the control box or PC, the MCPU 73 engages and disengages the clutch 72 and brake 76 to allow for rotational and reciprocal motion of the transducer 18 in the first elongate portion 12. Thus, to move the transducer 18 linearly along the guide 32 of the second connector 24, the clutch 72 is released and the brake 76 is applied. Conversely, to rotate the transducer 18 about the central axis 60 of the platform assembly 42, the clutch 72 is engaged and the brake 76 is released. Thus, when a physician activates the probe 10 using the control box or PC, the MCPU 73 will signal the clutch 72 and brake 76 to engage or disengage depending on the commands initiated by the physician.

The circuitry and electronics of the probe 10 preferably include a controller 83, a pulser/receiver 85, a digitizer 87, and a high speed data interface 89. The controller 83 receives commands from an external data processing system (e.g., a PC computer) 91 having a touch screen display 93 or other control dials and buttons via the data interface 89. These commands are used to configure both the pulser/receiver 85 and the probe 10. An acoustic pulse is generated in the pulser/receiver 85 and sent to the scanning probe 10 over a coaxial cable. Backscattered ultrasound data from the probe transducer 18 is processed by the receiver 85. The data is then digitized by the digitizer 87 and sent to a memory buffer in the controller 83. The data is then sent to the PC 91 for image formation on the touch screen display 93 via the data interface 89.

In response to operation command signals representing a first mode of operation received from the PC 91 via the high speed data interface 89, the controller 83 engages the clutch 72 and disengages the brake 76 to a low for rotational motion of the transducer 18 in the first elongate portion 12 while the transducer 18 remains longitudinally fixed relative thereto (the transmission system 46 is inoperable because the inner shaft 70 is rotatably fixed to the outer shaft 74). In response to operation command signals representing a second mode of operation received from the PC 91, the controller 83 disengages the clutch 72 and engages the brake 76 to allow for reciprocating translation of the transducer 18 in the first elongate portion 12 while precluding rotation of it relative thereto (the inner shaft 70 is disengaged from the outer shaft 74 and drives the transmission system 46, and the outer shaft 74 is prevented from rotating, which prevents rotation of the platform assembly 42 which is rotatably fixed to the outer shaft 74, and hence the transducer 18, which is rotatably fixed to the platform assembly 42). The controller 83 receives information on the position of the transducer 18 from a position tracker (not shown), which is connected to the probes rotational axis encoder 80 and linear axis encoder 78. Various embodiments of the electronics driving operation of the probe 10 can be utilized, including all of those disclosed in U.S. patent application Ser. No. 11/475,674 which has been incorporated herein by reference.

The improved probe 10 allows for controlled translational and rotational movement of the ultrasonic transducer 18 inside and across the substantially narrow distal scanning first elongate portion 12 of the probe's housing 11. The narrow distal scanning first elongate portion 12 facilitates positioning and orienting of the probe 10 at different angles within the patient about the prostate, and imaging and biopsying the prostate as discussed below. While two connectors are preferred for connecting to the transducer 18 to facilitate translation and rotation thereof, it will be appreciated that a single connector may be utilized which rigidly couples the transducer 18 to the movable member 44, provided that such single connector is sufficiently rigid to firmly maintain the radial position of the transducer 18 relative to the first elongate portion 12 of the housing 11 (e.g., provided the single connector does not bend). It is noted that a single connector should not be directly fixed to the frame 48 of the platform assembly 42 as it would need to translate with the movable member 44 relative to the frame 48. For example, the first connector 22 is sufficient to provide the aforementioned controlled movement to the transducer 18 without guide 32 and support 34 of the second connector 24 provided that the first connector 22 is fixed at both ends to the transducer 18 and movable member 44, does not bend, and will not bend over repeated use of the probe 10.

The improved transrectal ultrasonic probe 10 may be used in conjunction with various biopsy needles and delivery systems known in the art, including, for example, those disclosed in U.S. patent application Ser. Nos. 11/895,228 and 11/475,674, which are herein incorporated by reference in their entireties, as well as the improved biopsy needle and delivery system of U.S. patent application Ser. No. 12/834,384, which is herein incorporated by reference in its entirety.

Figure 9:
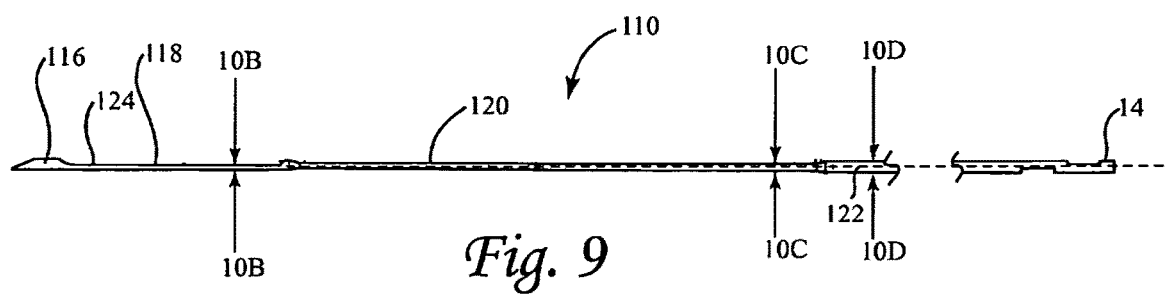
FIG. 9 is a broken side view of the biopsy needle.
Figure 10A:
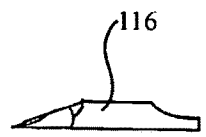
FIG. 10A is a side view of the tissue piercing distal end of the biopsy needle of FIG. 9.
Figure 10B:
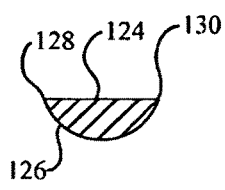
FIG. 10B is a longitudinal view of the cross section of the sampling section of the biopsy needle of FIG. 9.
Figure 10C:
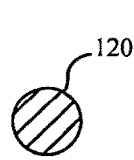
FIG. 10C is a longitudinal view of the cross section of the bending section of the biopsy needle of FIG. 9.
Figure 10D:
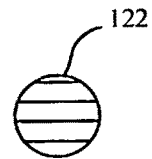
FIG. 10D is a longitudinal view of the cross section of the body portion of the biopsy needle of FIG. 9.

The preferred biopsy needle 110 and cannula 112 to be used in conjunction with the improved probe 10 are best seen with reference to FIGS. 9-11. As most clearly shown in FIGS. 9-10D, the needle 110 includes a proximal end, a tissue piercing distal end 116, a sampling section 118 proximal of the tissue piercing distal end 116 and having a flat top surface 124, rounded bottom surface 126, and ground down rounded edges 128, 130 on opposite sides of the top surface 124, a bending section 120 proximal of the sampling section 118 and preferably having a circular cross section, and a body portion 122 proximal of the bending section 120. The sampling section 118, bending section 120, and body portion 122 of the needle 110 are all preferably solidly and integrally formed with varying degrees of flexibility. The bending section 120 is preferably the most flexible portion of the needle 110.

The improved probe 10 may be used in conjunction with the needle 110, cannula 112, and guide assembly 111 in accordance with the biopsy procedure described in U.S. patent application Ser. No. 12/834,357. Alternatively, it will be appreciated that various other methodologies, embodiments, and additional equipment may be utilized with the improved probe 10 to procure a biopsy sample, including, for example, the methodologies, embodiments, and additional equipment described in U.S. patent application Ser. No. 11/895,228.

Figure 13:
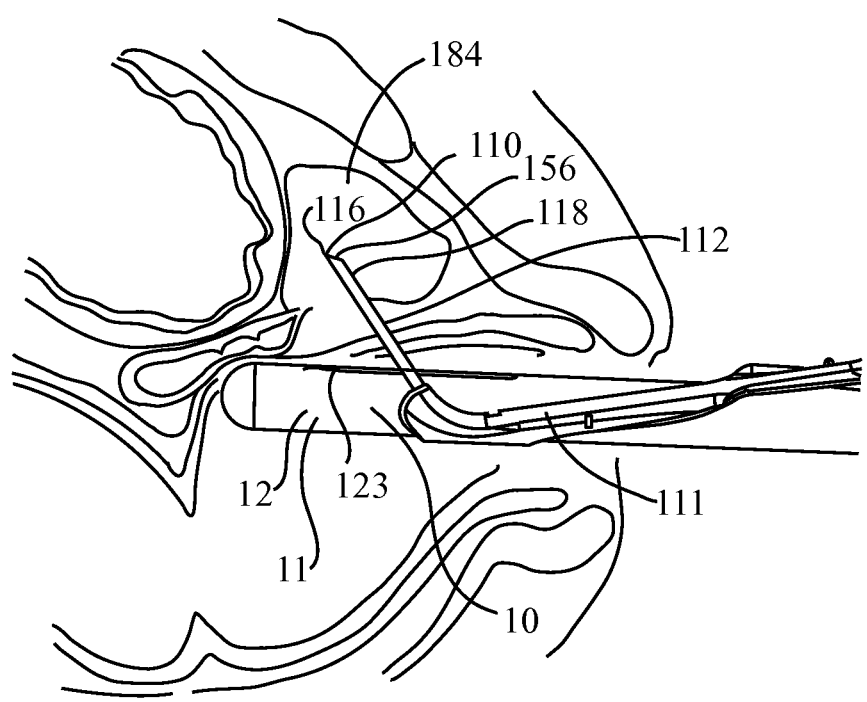
FIG. 13 is a schematic view of the biopsy needle, cannula, and guide assembly mounted on the first elongate portion of the probe of FIG. 1 and used to biopsy the prostate of a patient.
Figure 14A:
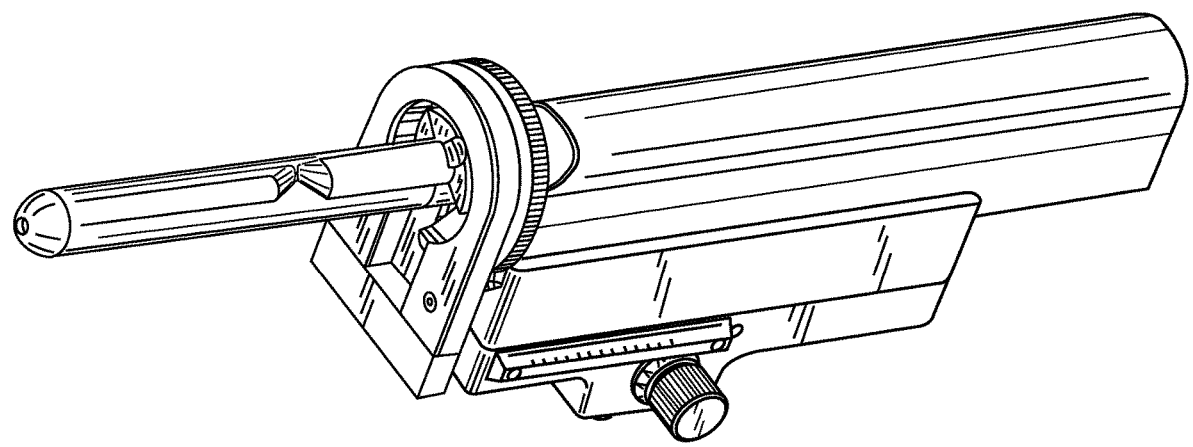
FIG. 14A is a perspective view of an ultrasonic probe known in the art.
Figure 14B:
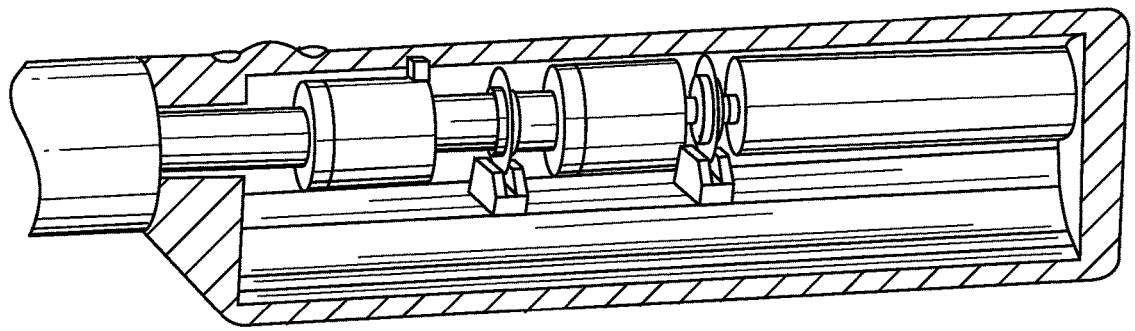
FIG. 14B is a side partially sliced view of a drive assembly known in the art.
Figure 14C:
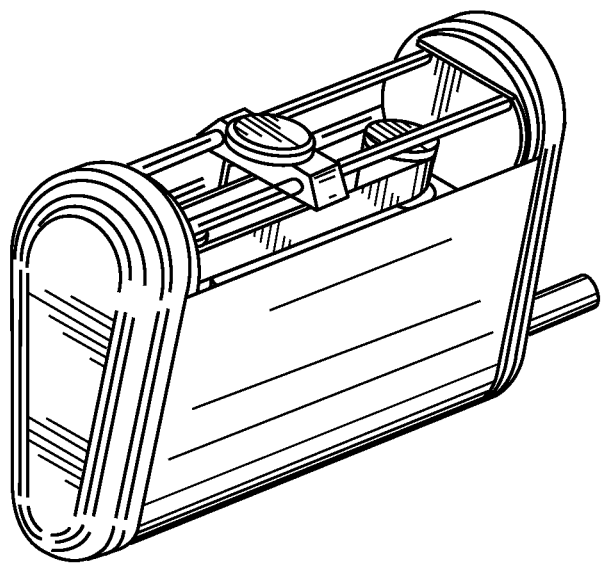
FIG. 14C is a perspective view of a platform assembly and movable member known in the art.
Figure 14D:
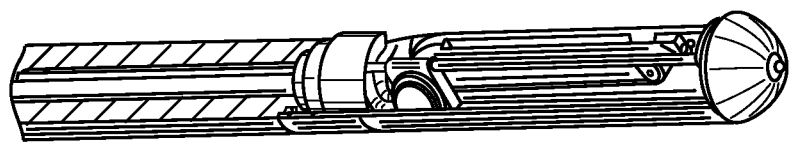
FIG. 14D is a cutaway view disclosing operative components of an ultrasonic probe known in the art.

Turning to FIGS. 1 and 13, the improved ultrasonic probe 10 and needle assembly (e.g., needle 110 and cannula 112) are used with a delivery system which includes the guide assembly 111 and the biopsy gun 107 to procure a tissue sample from the prostate 184 of a patient. The needle 110 and cannula 112 preferably at least partially disposed within and coupled to the biopsy gun 107. The narrow elongate distal scanning first elongate portion 12 of the improved probe 10 is inserted into the rectum of the patient adjacent the prostate 184 as shown n FIG. 13. As discussed above, the substantially small scanning first elongate portion 12 of the housing 11 facilitates insertion into the rectum, and positioning and orienting the probe 10 therein. The probe 10 is preferably held by a cradle in a fixed stationary position. Transrectal probes commonly used in the art can cause significant discomfort to the patient, and the inventors have found that the transrectal probe of U.S. application Ser. Nos. 11/895,228 and 11/475,674 also can cause discomfort to patients. The substantially narrow distal scanning first elongate portion 12 of the new improved probe 10 reduces this discomfort.

The guide assembly 111 is preferably attached to a guide/index collar 189 (FIG. 1) of the probe 10. The guide/index collar 189 controls radial and axial movement of the guide assembly 111 on the probe 10, and preferably orients the guide assembly 111 such that it straddles the probe 10 adjacent an imaging window 123 in the probe 10, and is sloped slightly downward at a ten degree angle. Alternatively, the guide assembly 111 may be fixed to the probe 10 and/or oriented horizontally relative thereto. Ultrasonic images of the prostate 184 are received through the imaging window 123, unobstructed by the guide assembly 111.

Figure 12A:
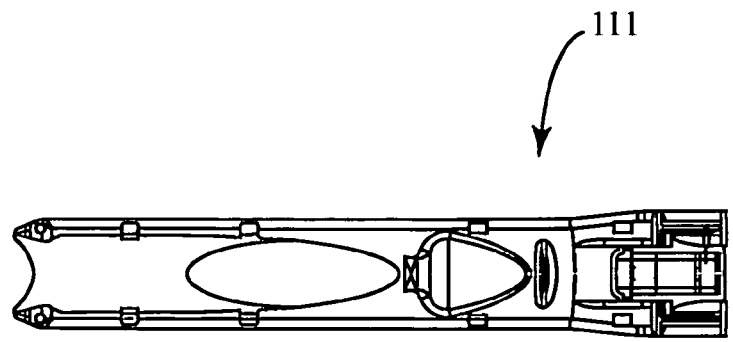
FIG. 12A is a top view of the guide assembly.
Figure 12B:
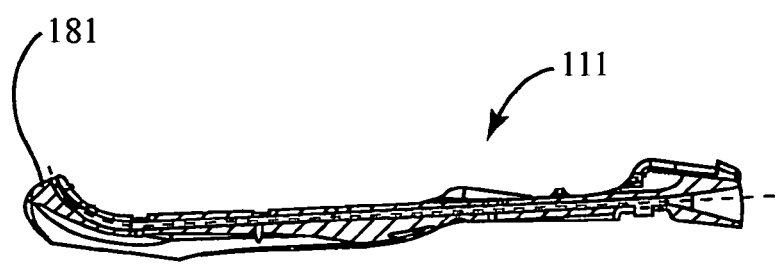
FIG. 12B is a side view of the guide assembly of FIG. 12A.

Once the probe 10 and guide assembly 111 are properly positioned within the patient, the respective distal ends 116, 156 of the needle 110 and cannula 112 are advanced together through the inlet of the guide assembly 111 and are guided to a fixed orientation and direction at the outlet 181 (FIG. 12B) of the guide assembly 111 to place the needle 110 and cannula 112 in a bent configuration within the patient adjacent the prostate 184.

Once the needle 110 and cannula 112 are in a bent configuration and the respective distal ends 116, 156 of the needle 110 and cannula 112 are disposed adjacent the prostate 184, the biopsy gun 107 is fired to advance the needle 110 from the bent configuration into the prostate 184 of the patient. During this first firing, the sampling portion 118 of the needle 110 rapidly advances out of the cannula 112 into the prostate over a stroke length which is preferably approximately equal to the length of the sampling section 118. A second firing of the biopsy gun 107 causes the cannula 112 to fire and advance over the exposed sampling section 118 of the needle 110 in the prostate 184, capturing sample tissue therein between the cannula 112 and the needle 110.

The needle 110 and cannula 112 are then withdrawn from the patient with the tissue sample captured within the cannula 12, and the process is repeated as needed with the improved probe 10 remaining in the patient. It will be appreciated that the narrower distal elongate portion 12 of the housing 11 of the new probe 10 allows for easier manipulation inside of the patient to different positions and orientations.

Figure 15:
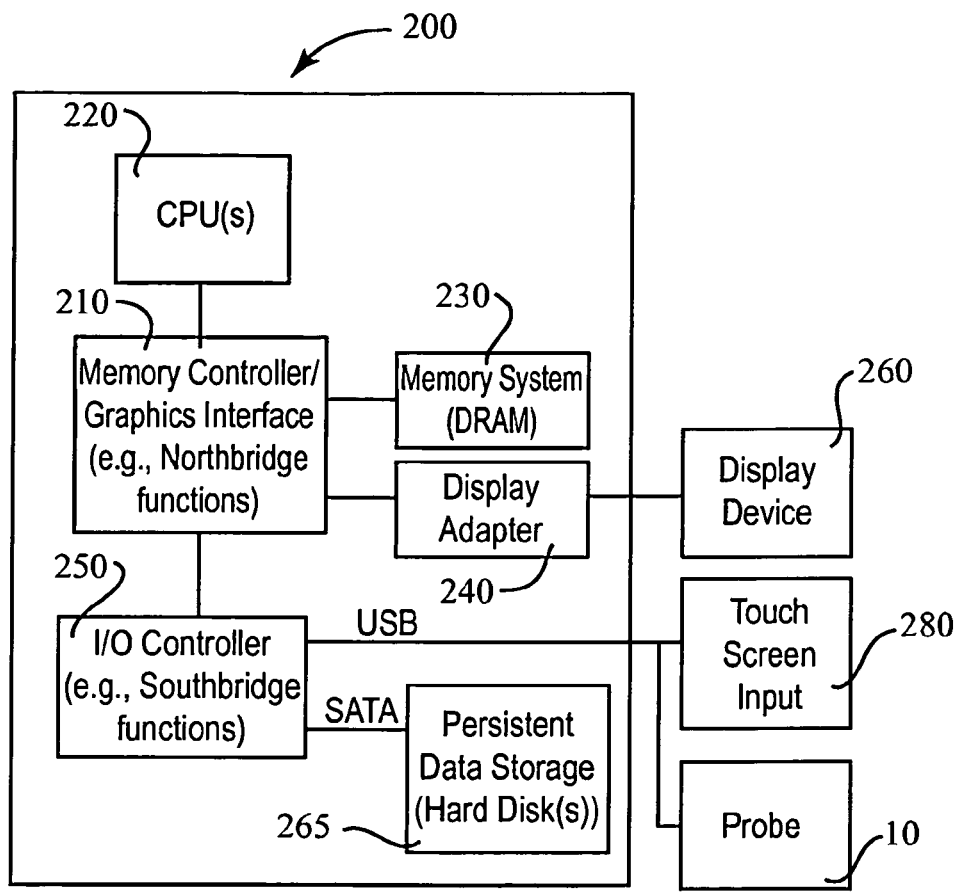
FIG. 15 is a schematic block diagram of a preferred embodiment of the data processing system of the invention.

Turning to FIG. 15, an exemplary data processing apparatus, such as the data processing system 200, includes a memory controller and graphics interface 210 that interface between a memory system 230 and one or more CPU(s) 220. Interface 210 also interfaces to a display adapter 240 that generates and outputs display windows for display on a display device 260 connected thereto. An input/output controller 250 provides an interface (USB interface) to an imaging device, such as the probe 10, and to an input device, such as a touch screen input device 280 that overlays the display screen of the display device 260. The touch screen input device 280 can be a separate unit that is attached and secured to the display device 260 (or can be integrally formed as part of the display device 260). The input/output controller 250 also provides an interface (e.g. SATA) to a data storage medium, such as a hard disk 265, for data storage. The hard disk 265 stores software logic loaded into the memory system 230 for execution by the CPU(s) 220. The software logic preferably maintains an linage buffer for storing two dimensional image data derived from sagittal and transverse scan planes of the target tissue (e.g., prostate). As shown in FIGS. 17-19B, the display device 260 of the data processing system 200 displays biopsy information and various on-screen controls for touch input by an operator via the touch-screen input device 280 as further discussed below.

Figure 16A:
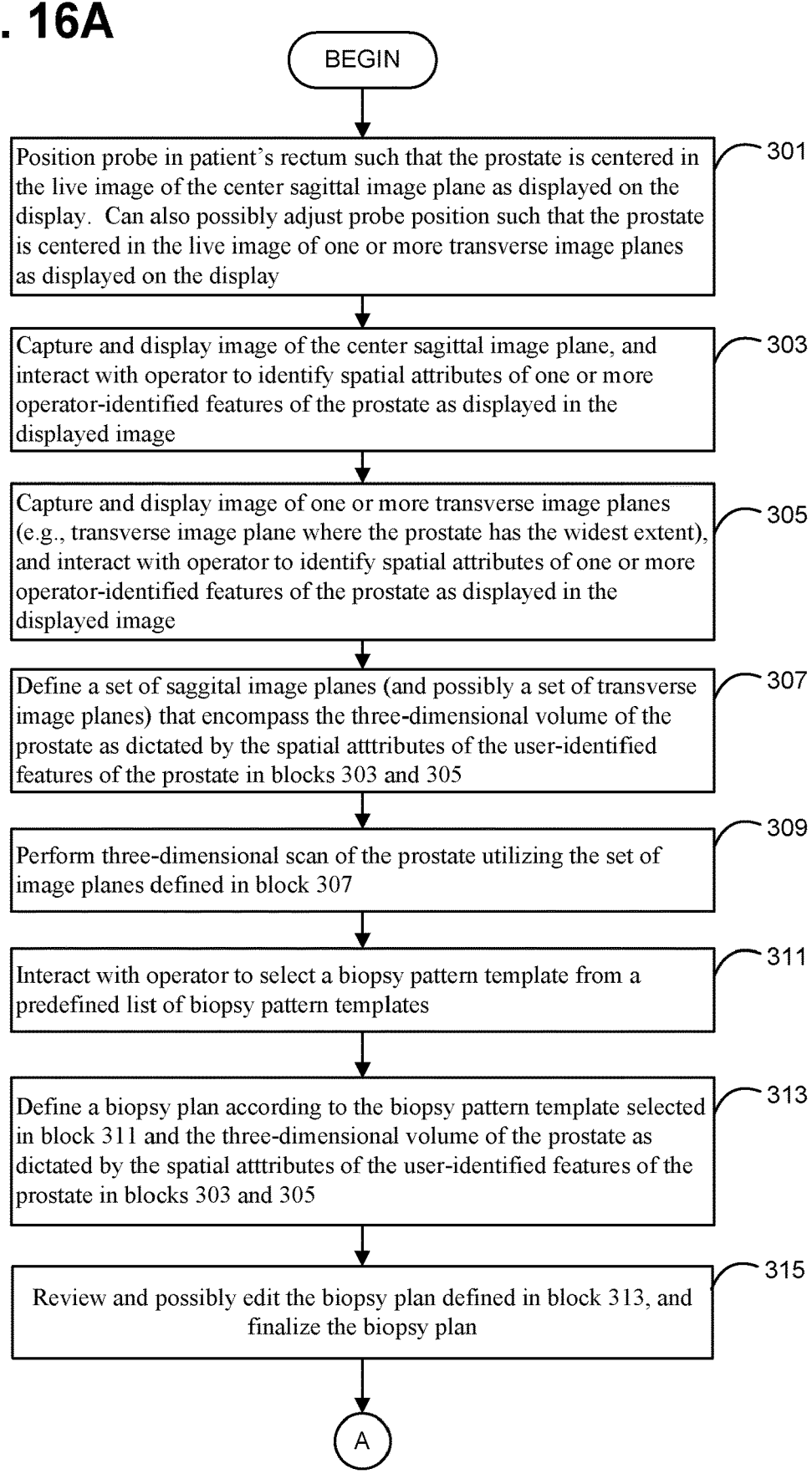
FIGS. 16A and 16B, collectively, contain a flow chart illustrating operations carried out by the system of FIG. 15 for biopsy of the prostate of a patient in accordance with the present invention; the operations interact with an operator to mark various features of the prostate, image the prostate, and define a biopsy plan (FIG. 16A); a series of biopsy samples are procured in accordance with the biopsy plan while monitoring and adjusting for patient movement (FIG. 16B).
Figure 16B:
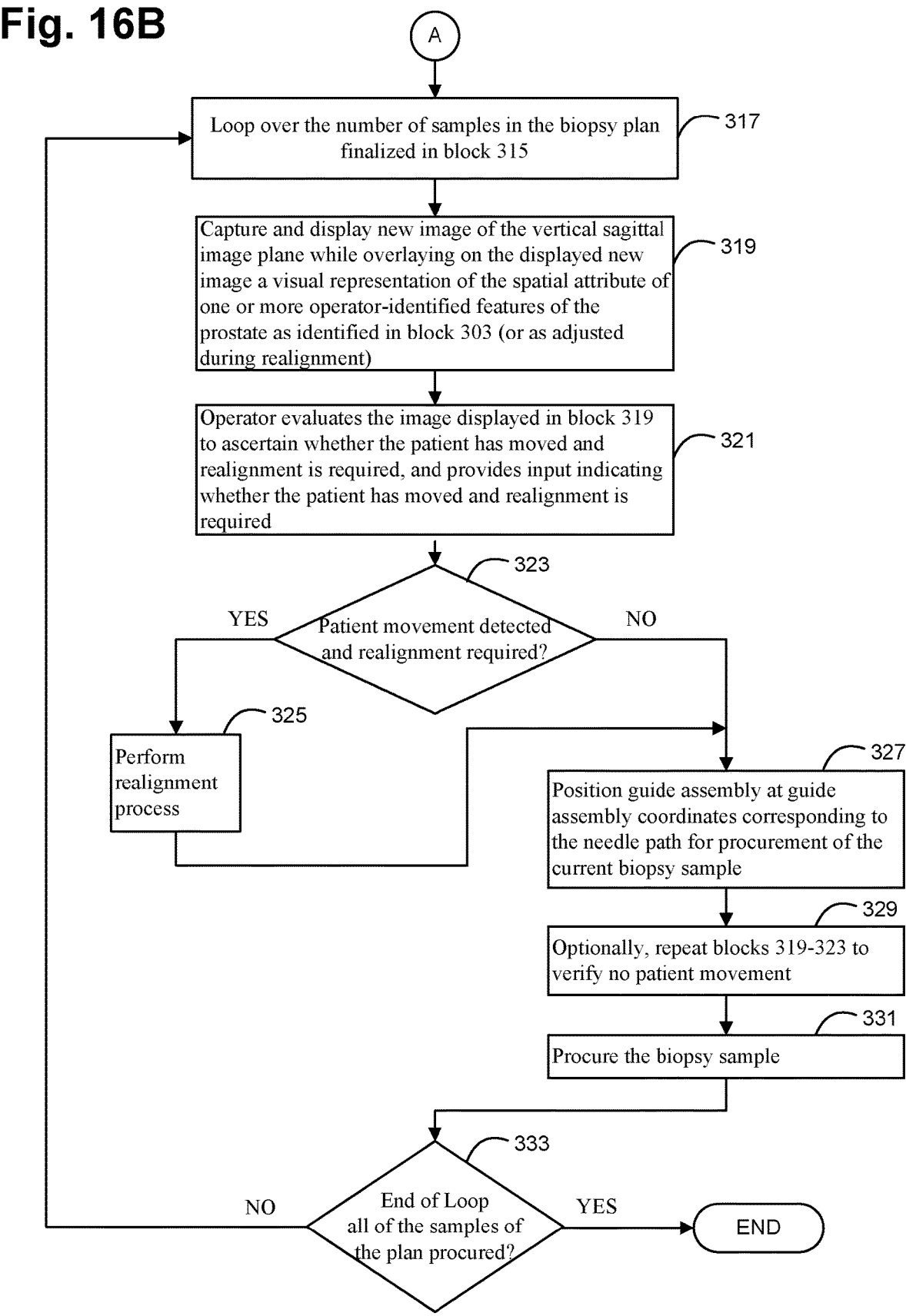
Figure 17:
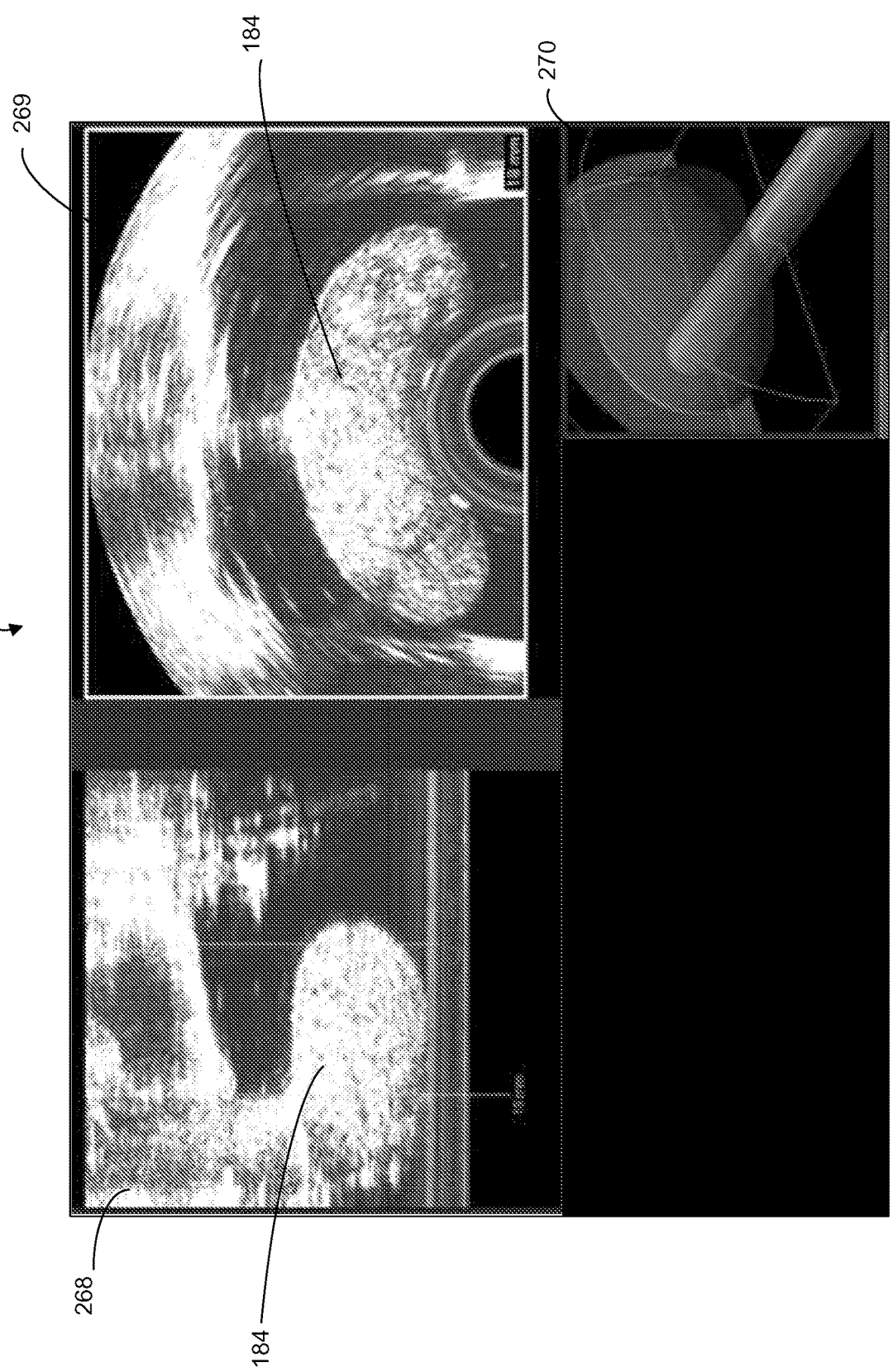
FIG. 17 is a schematic of an exemplary graphical user interface displayed on the display device of the system of FIG. 15.

Turning to FIGS. 16A and 16B the data processing system 200 interacts with the operator to identify spatial attributes of various features of the prostate (referred to herein as operator-assisted feature localization), scan the prostate, define a biopsy plan, and procure biopsy samples of the prostate in accordance with the biopsy plan while monitoring and adjusting for patient movement.

Initially, at block 301, the probe 10 is positioned in the patient's rectum while the system 200 displays live sagittal and transverse images of the prostate 184. Sagittal images are displayed in a sagittal display window 268 (FIGS. 17 and 18A) of the display device 260 and transverse images are displayed in a transverse display window 269. A visual representation of the live imaging plane is superimposed on a three-dimensional graphical representation of a typical prostate gland in a viewport display window 270 (FIGS. 17 and 18A) of the display device 260 as taught in U.S. Patent Appl. Publ. No. 2008/0146933, commonly assigned to assignee of the present invention and herein incorporated by reference in its entirety. The operator can control the imaging probe 10 and display to move to another live sagittal image plane or another live transverse image plane by touch input or other suitable user input controls. For example, in the preferred embodiment, the operator can move to a live sagittal image plane by touching the transverse display window 269 at a user-selected point. In this case, the imaging probe 10 automatically scans the sagittal image plane that passes through the user-selected point dictated by the touch input, the sagittal display window 268 is updated to display the image data of the scanned sagittal imaging plane as captured by the probe, and the viewport display window 270 is updated to show a visual representation of the new live sagittal plane superimposed on the three-dimensional graphical representation of a typical prostate gland. Similarly, the operator can move to a live transverse image plane by touching the sagittal display window 268 at a user-selected point. In this case, the imaging probe 10 automatically scans the transverse image plane that passes through the user-selected point dictated by the touch input, the transverse display window 269 is updated to display the image data of the scanned transverse imaging plane as captured by the probe, and the viewport display window is updated to show a visual representation of the new live transverse imaging plane superimposed on the three-dimensional graphical representation of a typical prostate gland. In the illustrative embodiment, the operator utilizes the live sagittal and transverse images of the prostate to center the probe 10. Preferably, the operator adjusts the probe 10 until the live images of the prostate show the prostate 184 centered in a center sagittal image plane displayed in the sagittal display window 268, and possibly also centered in one or more live transverse images displayed in the transverse display window 269. As discussed above, the term 'center sagittal image plane' is used herein to refer to the sagittal image plane which passes through the approximate center of the prostate 184 and thus divides the prostate into two halves. Once centered, the probe 10 is preferably held by a cradle in a fixed stationary position.

At block 303, with the probe fixed in a stationary position such that the live images of the prostate appear centered in the center sagittal image plane (and preferably also in a transverse image plane), the operator touches a button on the display device 260. The system 200 then scans, captures, stores, and displays an image of the center sagittal image plane in the sagittal display window 268 and interacts with the operator to identify various spatial attributes of one or more operator-identified features of the prostate which appear in the sagittal image displayed in the display window 268.

Figure 18A:
FIG. 18A is a graphical user interface displayed on the display device of the system of FIG. 15 that provides for operator input in marking a spatial attribute of the base of the prostate.
Figure 18B:
FIG. 18B is a graphical user interface displayed on the display device of the system of FIG. 15 that provides for operator input in marking a spatial attribute of the apex of the prostate.

For example, as shown in FIG. 18A, the system 200 interacts with the operator to identify a spatial attribute of the base 362 of the prostate by displaying a vertical line 364 (labeled "B" in FIG. 18A) overlaid upon the sagittal image of the center sagittal image plane in the sagittal display window 268. The operator can adjust the horizontal position of the vertical line 364 by touch input (or by manipulation of fine adjustment buttons (not shown) or other suitable user input controls) such that it intersects the base 362 of the prostate as displayed in the sagittal display window 268. The system 200 identifies and stores the 'x' pixel coordinate of the operator-positioned vertical line 364 after it has been located at the base 362. In this manner, the 'x' pixel coordinate of the operator-positioned vertical line 364 represents data corresponding to the operator-inputted spatial attribute of the base of the prostate.

Similar operations can be performed to identify a spatial attribute of the apex 366 of the prostate by displaying a vertical line 368 (labeled "A" in FIG. 18B) overlaid upon the sagittal image of the center sagittal image plane in the sagittal display window 268. The operator can adjust the horizontal position of the vertical line 368 by touch input (or by manipulation of fine adjustment buttons (not shown) or other suitable user input controls) such that it intersects the apex 366 of the prostate as displayed in the sagittal display window 268. The system 200 identifies and stores the 'x' pixel coordinate of the operator-positioned vertical line 368 after it has been located at the apex 366. In this manner, the 'x' pixel coordinate of the operator-positioned vertical line 368 represents data corresponding to the operator-inputted spatial attribute of the apex of the prostate.

In other embodiments, the vertical line used to define the spatial attribute of a given feature of the prostate can be substituted with (or complimented by) other suitable visual position indicators, such as an 'X', a bull's eye, or other visual mark or icon overlaid on the display window 268. The operator may interact with the system 200 by touch input or alternatively by use of a mouse, tracking ball, keyboard entries, etc., to properly position the vertical line, on-screen cursor, or other indicator.

As part of block 303, the system 200 can also interact with the operator to input spatial attributes representing the length of the prostate (which extends from the bladder neck to the apex of the prostate), and to derive data representing the length of the prostate from the operator-inputted spatial attributes. The system 200 also preferably interacts with the operator to input the spatial attributes of the anterior and posterior edges of the prostate in the sagittal display window 268, to store data corresponding to these marked spatial attributes, and to calculate the height of the prostate from this stored data.

At block 305, the system 200 scans, captures, stores, and displays a single transverse image of the center transverse image plane in the transverse display window 269 and interacts with the operator to identify various spatial attributes of one or more operator-identified features of the prostate which appear in the transverse image displayed in the transverse display window 269. For example, the system 200 may interact with the operator to select the "widest" transverse imaging plane where the cross sectional profile of the prostate is the widest. The operator may toggle through various live transverse images of different transverse planes through the prostate and select the widest one. The system 200 then interacts with the operator to mark the prostate's leftmost and rightmost peripheral projections in this "widest" transverse imaging plane displayed in the transverse display window 269 using a vertical line, an indicator, etc. as discussed above. The system 200 stores data corresponding to the operator inputted and marked spatial attributes of the prostate's leftmost and rightmost peripheral projections in the "widest" transverse imaging plane of the prostate and calculates the width of the prostate from the stored data.

Figure 18C:
FIG. 18C is a graphical user interface displayed on the display device of the system of FIG. 15 that provides for operator input in marking a spatial attribute of the right angular boundary of the prostate.

As part of block 305, the system 200 can interact with the operator to input angular scanning limits of the probe 10 (e.g., the right and left angles relative to the centerline of the probe which represent the angular limits through which the probe 10 must scan in order to scan the prostate in its entirety). For example, the operator can designate the right scanning angle by displaying a line 370 overlaid upon the transverse image of the transverse image plane displayed in the transverse display window 269 as shown in FIG. 18C. The operator can adjust the rotational orientation of the line 370 by touch input (or by manipulation of fine adjustment buttons (not shown) or other suitable user input controls) such that it intersects the right angular boundary of the prostate as displayed in the transverse display window 269. The system 200 identifies and stores the rotational angle of the operator-positioned line 370 after it has been located at the right angular boundary of the prostate. Similar operations can be performed for the left scanning angle. In this manner, the rotational angles of the operator-positioned lines represents data corresponding to the angular limits through which the probe 10 must scan in order to scan the prostate in its entirety. It will be appreciated that transverse image data in multiple transverse planes (in additional to the 'widest' transverse plane) may need to be viewed in the transverse display window 269 in order to ensure that the true angular limits of the prostate have been captured.

Figure 18D:
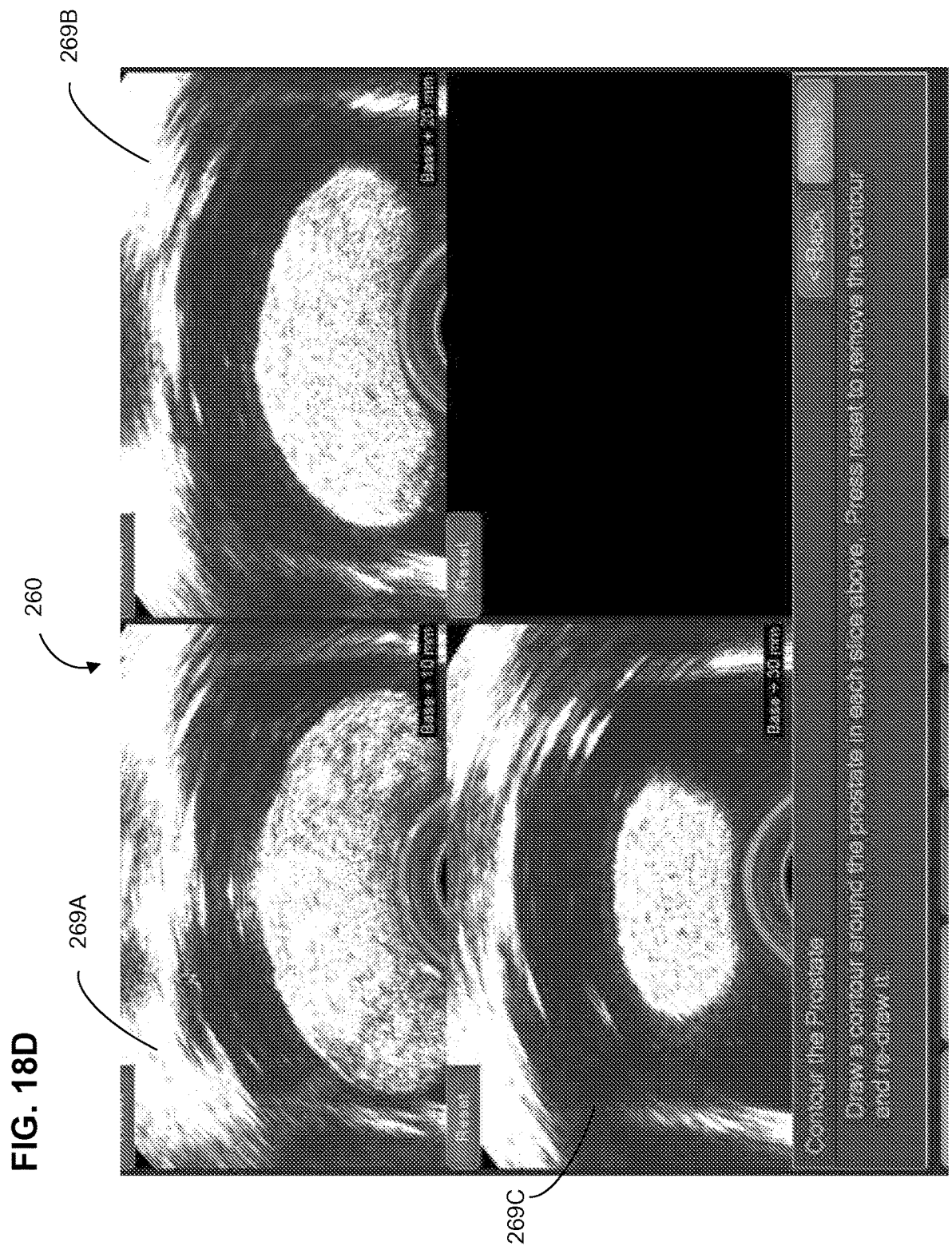
FIG. 18D is a graphical user interface displayed on the display device of the system of FIG. 15 that provides for operator input in marking the contour of the prostate.

As part of block 305, the system 200 may also interact with the operator to input a contour around the prostate in various transverse images 269A, 269B, 269C of the prostate displayed on the display device 260 as shown in FIG. 18D. Such contours may be drawn around the outer border of prostate appearing in the images by touch input of the operator, or by other input as discussed above. The system 200 stores these spatial attributes of the prostate as well.

It will be appreciated that the system 200 can derive the length, width, and height of the prostate as discussed above with respect to blocks 303 and 305 by maintaining various coordinate systems (e.g., a display coordinate system, probe coordinate system (see Xc, Yc, Zc of FIG. 2), guide assembly coordinate system, etc.) as well as transformations therebetween. For example, the system 200 can calculate the length of the prostate in the probe coordinate system of FIG. 2 by transforming the 'x' pixel coordinate values of the operator adjusted vertical lines depicting the relative locations of the bladder neck and apex to corresponding positions in the probe coordinate system utilizing a transformation between the display coordinate system of the display device 260 and the probe coordinate system, and then subtracting the resultant coordinates.

It will be appreciated that data corresponding to operator-inputted spatial attribute(s) of a feature can be defined and stored in one or more of these coordinate systems. From the length, width, and height of the prostate, the system 200 can calculate the volume of the prostate, preferably using these values in conjunction with a suitable empirical model.

It will also be appreciated that the features marked by the operator at blocks 303 and 305, as well as additional features marked by the operator, if any, are preferably common, easily identifiable features and discriminative of prostate position over a wide range of patients. It is also contemplated that in addition to the modes of operator input described above, the operator may provide touch input to the data processing system 200 via a virtual keypad displayed on one of the display windows 268, 269 of the touch-screen display 260. Other suitable user interface mechanisms can also be utilized. The operator-inputted spatial attributes of each feature are stored by the software and memory controller 210, preferably on the hard disk 265 or in other suitable data storage medium.

At block 307, the system 200 defines a set of image planes that are distributed over the three-dimensional volume of the prostate as dictated by the spatial attributes of the operator-identified features of the prostate at blocks 303 and 305. The scan planes can include sagittal scan planes sampled at a regular angular spacing and/or transverse scan planes sampled at a regular depth spacing. In the preferred embodiment, the three dimensional scan volume of the prostate resembles a truncated cylinder which is bounded by oppositely facing transverse planes (passing through the bladder neck and apex of the prostate) and by sagittal planes passing through the left and right angular limits inputted by the operator at block 305.

At block 309, the system 200 conducts a full three dimensional scan of the prostate using the scan planes defined in block 307. In the preferred embodiment, the full three-dimensional scan uses a series of sagittal scan planes sampled at a regular angular spacing and/or transverse scan planes sampled at regular depth spacing. If only one of such two sets of data is taken or available, then one may be interpolated from the other. The software logic maintains an image buffer for storing the two dimensional image data derived from the sagittal and/or transverse scan planes of the prostate.

Figure 18E:
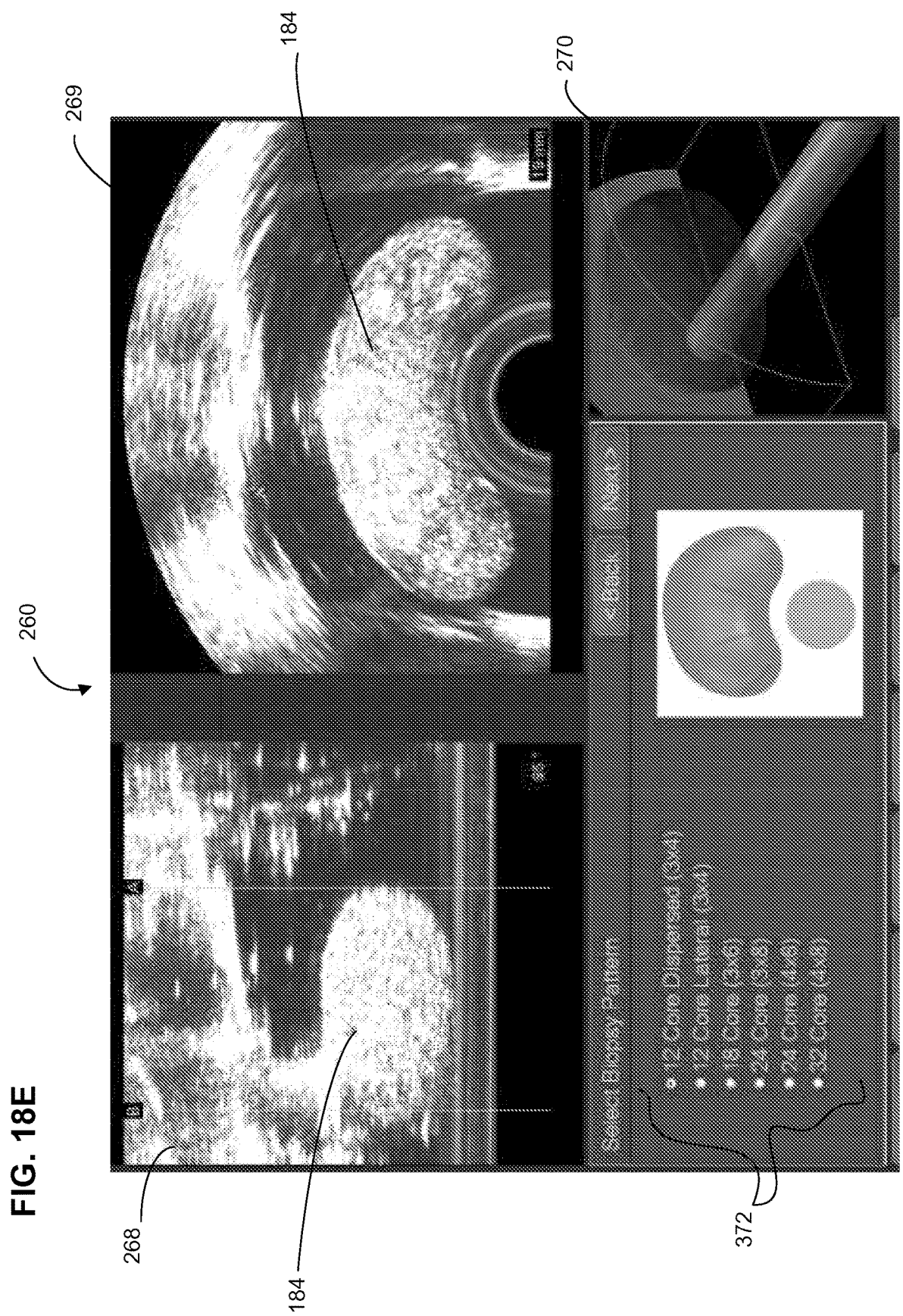
FIG. 18E is a graphical user interface displayed on the display device of the system of FIG. 15 that provides for operator input in selecting a particular biopsy pattern.

At block 311, the data processing system 200 derives a plurality of biopsy patterns 372 (FIG. 18E). The patterns vary in terms of the total number of samples (e.g., between twelve and thirty-two as shown in FIG. 18E) and the distribution of the samples through the prostate. The biopsy patterns 372 can target areas of the prostate where cancer is most likely to be found and are preferably based on accepted biopsy practice. The system 200 interacts with the operator to select one of the biopsy patterns. For example, as shown in FIG. 18E, the system 200 can display the plurality of biopsy patterns 372 at the lower left portion of the display 260 and provide operator controls for selecting one of them.

At block 313, after operator selection (or possibly in advance of such operator selection) of a particular biopsy pattern at block 311, the system 200 automatically derives a biopsy plan corresponding to the selected biopsy pattern. The biopsy plan includes needle paths (i.e., a direction and distance) through which the needle assemblies will be advanced to procure the desired biopsy samples of the prostate, as well as longitudinal and rotational coordinates for positioning the needle guide assembly such that it directs the needle assembly along the respective needle paths as further discussed below. The needle paths are preferably derived by the data processing system 200 according to the operator-selected biopsy pattern. In the preferred embodiment, the system 200 derives the needle paths of the biopsy plan based on the size of the prostate and the particular biopsy pattern selected in block 311 (e.g., number of samples and desired distribution of the samples). The system 200 is also optionally configurable to allow the operator to create, add and/or remove needle paths to/from the biopsy plan. These decisions may be based on knowledge gleaned from prior scans and procedures and/or from current images of the prostate.

Figure 18F:
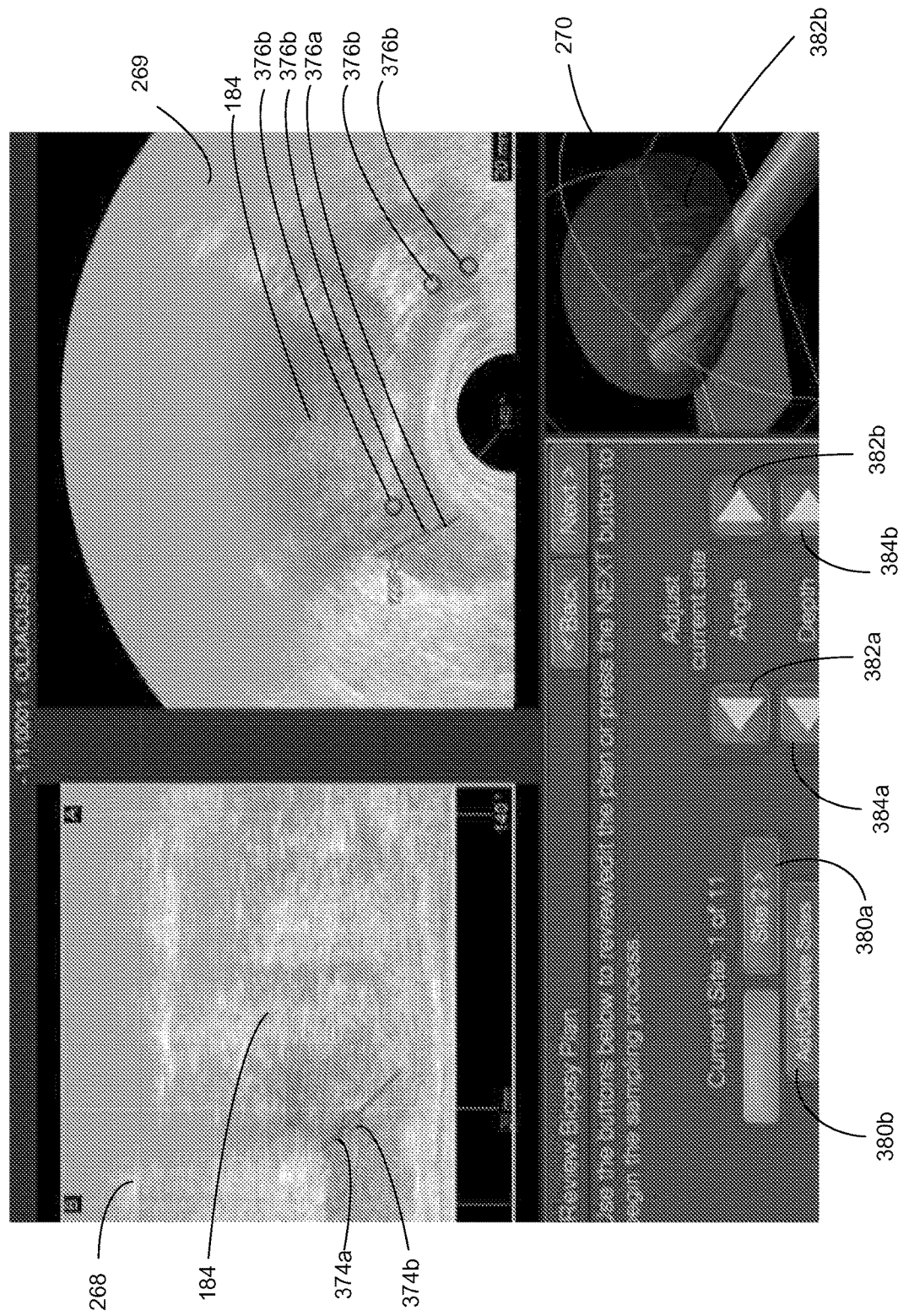
FIG. 18F is a graphical user interface displayed on the display device of FIG. 15 that provides for operator visualization of the locations of needle paths of a given biopsy plan carried out by the system of FIG. 15.

In block 315, the operator interacts with the system 200 to visualize and review the needle paths of the biopsy plan defined in block 313, and provide an indication that the needle path is complete or finalized. In the preferred embodiment, the system 200 is configured with user input controls such that the operator can sequence through the samples/needle paths of the plan to visualize the location of the samples/needle paths of the plan and make adjustments to the needle paths of the plan and/or delete or add needle paths to the plan as desired. For example, FIG. 18F shows touch input control 380*a* that enables the operator to sequence through the needle paths/samples of the plan and touch input control 380*b* that enables the operator to add or delete needle paths/samples from the plan. Touch input controls 382*a*, 382*b* allow the operator to adjust the angle of the current needle path, and touch input controls 384*a*, 384*b* allow the operator to adjust the depth of the current needle path. The viewport display window 270 may also be adapted to display lines representing the needle paths of the plan superimposed on the 3D representation of the typical prostate as shown in FIG. 18F. For needle path visualization, the projection of each respective needle path onto the sagittal image plane displayed in the sagittal display window 268 can be shown as a line 374*a* superimposed on the sagittal image displayed in the sagittal display window 268 and/or a circle 374*b* (or other suitable indicia) that indicates the location where the respective needle path intersects the sagittal image plane displayed in the sagittal display window 268 as shown in FIG. 18F. Similarly, the projection of each respective needle path onto the transverse image plane displayed in the transverse display window 269 can be shown as a line 376*a* superimposed on the transverse image displayed in the transverse display window 269 and/or a circle 376*b* (or other suitable indicia) that indicates the location where the respective needle path intersects the transverse image plane displayed in the transverse display window 269. In the preferred embodiment, each respective needle path corresponds to a vector in the probe coordinate system (FIG. 2). In the sagittal display window 268, line 374*a* is displayed for the respective needle path by projecting the needle path vector onto the sagittal image plan and displaying the resultant projected line.

In block 315, the operator can select a given needle path of the plan and the display device 260 may indicate the selected needle path by, for example, changing the color of the appropriate line and circle for the selected needle path. The operator may add a specific needle path to the biopsy plan, such as by selecting an on-screen button. Each time a needle path is selected, the displays windows 268, 269 and 270 are updated accordingly. The operator may also remove a specific needle path from the biopsy plan as described above. Once the operator has finished adding or removing needle paths from the selected biopsy plan, the operator indicates that the plan is complete and the plan data is persistently stored on the hard disk 265.

In block 317, the data processing system 200 interacts with the operator at block 317 to begin procuring biopsy samples in accordance with the biopsy plan finalized in block 315. The system 200 may also be adapted to allow the operator to modify the biopsy plan at any time in the process, either by adding or canceling needle paths. The operations perform a loop (blocks 317 to block 333) over the number of samples in the biopsy plan.

Figure 18G:
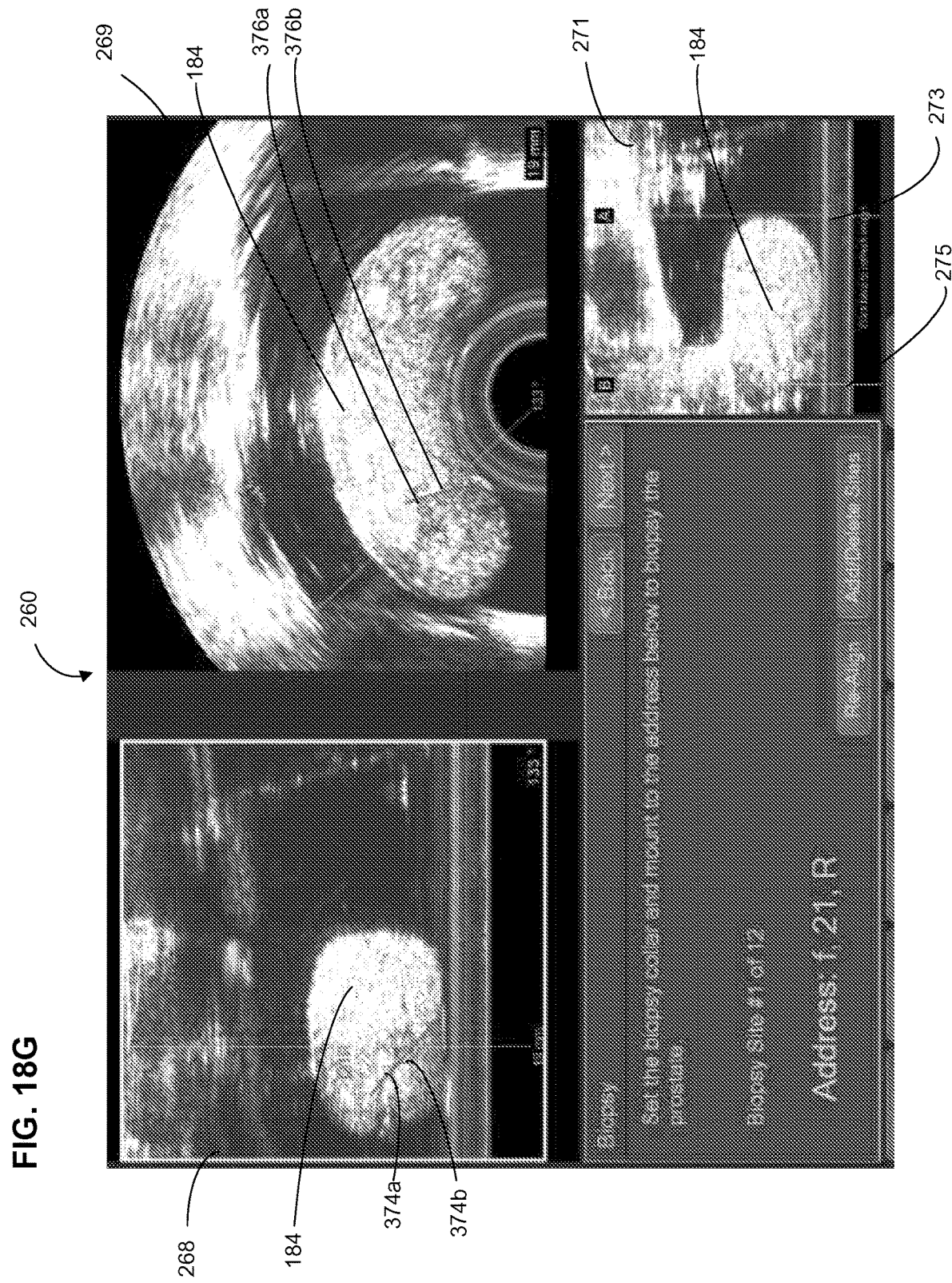
FIG. 18G is a graphical user interface displayed on the display device of FIG. 15 that provides for operator-assisted detection of patient movement during the procurement of biopsy samples of a given biopsy plan.

At block 319, the system 200 controls the probe 10 to rescan at least one of the predetermined image planes (e.g., the center sagittal image plane and/or the transverse image plane where the prostate is the "widest") previously scanned and "marked" by the operator as part of the operator-assisted feature localization process of blocks 303 and/or 305. The system 200 displays the refreshed (new) image data of the predetermined image plane(s) as captured by the rescanning of the probe 10 in a predefined display window of the display device 260, and superimposes a graphical representation (e.g., a vertical line, an icon, or other display element) of one or more of the operator-inputted spatial attributes of a feature (inputted at blocks 303, 305, or during realignment of the probe 10 as further discussed below) on the predefined display window at a corresponding display window location. For example, FIG. 18G shows a predefined display window 271 that displays the refreshed image data of the center sagittal image plane. A vertical line 273 is superimposed on the image displayed in the display window 271 at window coordinates corresponding to the operator-marked spatial attribute of the apex derived in block 303 as described above (FIG. 18B). A vertical line 275 is superimposed on the image displayed in the display window 271 at window coordinates corresponding to the operator-marked spatial attribute of the base derived in block 303 as described above (FIG. 18A).

At block 321, the operator visually compares the current spatial attributes of the operator-marked feature(s) to the previously inputted operator-marked spatial attributes(s) of the feature(s) in the predefined display window. For example, turning to FIG. 18G, the position of the apex and base of the prostate 184 can be visually evaluated in the display window 271 by determining whether either one (or both) of the vertical lines 273, 275 have shifted relative to the apex and base of the prostate appearing in the center sagittal image displayed in display window 271. If so, then such misalignment indicates that the patient has moved longitudinally relative to the probe 10 (depth-wise) since the last scan of the predetermined image plane (e.g. the center sagittal plane). Other suitable visualizations can be used to detect patient movement as part of block 323. For example, the operator can evaluate whether the patient has rotated relative to the probe 10 since the last scan of the center transverse plane by evaluating whether the contour of the prostate in a refreshed image of a predetermined transverse imaging plane (e.g., the center transverse image) aligns with the location of the prostate contour inputted by the operator either at block 305 (or possible input by the operator during realignment of the probe in block 325).

In the event that the operator has visually detected patient movement (depth or rotation) in block 323, the operator can initiate a realignment process at block 325. If instead no patient movement is detected or no realignment is required, then the operations proceed to blocks 327 to 331 as described below.

At block 325, a realignment process is carried out that corrects for patient movement by realigning the probe or by inputting to the system 200 the new spatial attributes of the particular features of the prostate. The advantage of such adjustment is that it allows the operator to continue with the biopsy procedure to capture biopsy samples of the prostate at the specific locations desired in accordance with the biopsy pattern selected at block 311 and the biopsy plan derived at blocks 313 and 315. It will be appreciated that absent such adjustment, the operator would need to either restart the whole process or continue collecting biopsy samples knowing that the actual sample locations will not be exactly where intended.

Figure 19A:
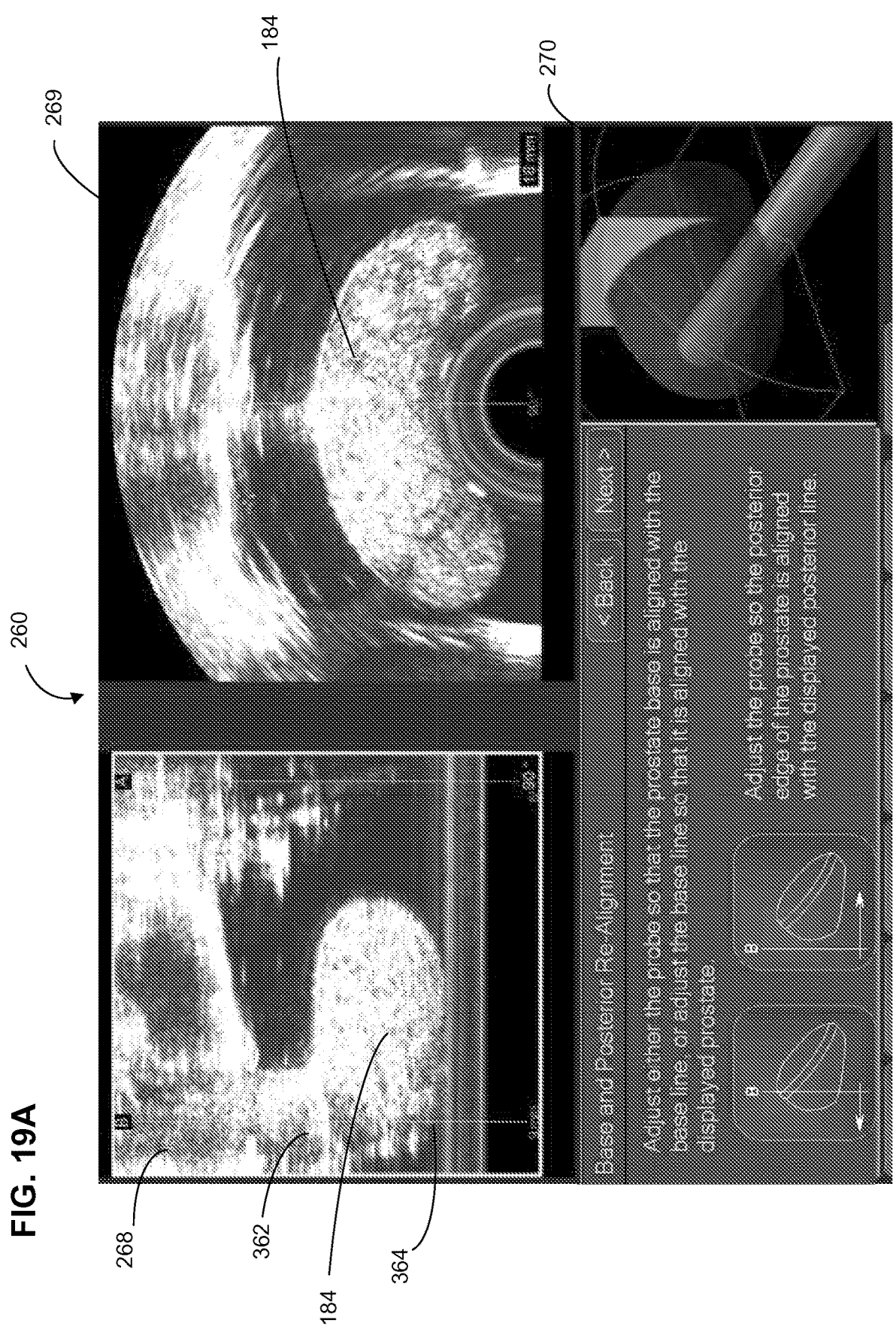
FIG. 19A is a graphical user interface for repositioning of the probe and needle guide assembly (or an operator-inputted spatial attribute of a feature of the prostate) in order to correct for longitudinal movement of the patient relative to the probe.

In block 325, one method of realignment is to mechanically adjust the longitudinal and/or rotational position of the probe. If the patient has moved in the longitudinal direction of the probe (i.e., depthwise within the rectum), then the probe 10 may be moved in a longitudinal direction opposite the direction that the patient has moved. In order to aid the operator in realigning the probe, the probe can be controlled to scan the center sagittal scan plane, and the refreshed center sagittal image can be displayed in the sagittal display window 268 along with the previously inputted operator-marked spatial attributes(s) of the feature(s) of the prostate (e.g., vertical lines for the base and apex of the prostate) as shown in FIG. 19A. Such scan/center sagittal image refresh operations can be triggered by operator control, for example, by touch screen input. These operations can be repeated until the operator sees alignment between the current spatial attribute(s) of the features in the refreshed image and the previously inputted spatial attributes. Alternatively, the operator can readjust the spatial attributes of the features on-screen, for example by user-input controls that shift the vertical lines for the base and apex of the prostate. By way of another example, the operator can adjust the rotational alignment of the probe 10 until the outer edges of the prostate in the transverse image fall within the contour 371 as shown in FIG. 19B. Alternatively, the operator can readjust the spatial attributes of the features on-screen, for example by user-input controls that rotate the contour of the prostate. When the realignment process is complete, the system 200 re-calculates the longitudinal and rotational coordinates of the needle guide assembly 111 for the remaining needle paths of the biopsy plan based on the shift in operator-defined spatial attributes of the features and the position and orientation of the probe in the aligned configuration. It will be appreciated that in the case of rotational movement, either the probe 10 or the transducer 18 will need to be rotated so as to capture the center sagittal plane previously scanned. The system 200 may simply rotate the transducer 18 to realign it with the center transverse plane rather than instructing the operator to rotate the probe body 10.

It will be appreciated that the realignment process of block 325 may be used to align different feature(s) of the prostate with various pre-defined operator-marked spatial attribute(s) in the touch-screen display 260. Importantly, if the realignment process involved updating the spatial attributes on-screen rather than adjusting the probe 10, the system 200 updates the stored data corresponding to the spatial attributes of the features (e.g., replaces or supplements the data entered at blocks 303 and 305 with data corresponding to the new spatial attributes of the features as inputted by the operator). Once realignment is completed, the system 200 continues to blocks 327 to 331.

At block 327, the operator positions the needle guide assembly 111 at longitudinal and rotational coordinates which correspond to the current needle path of the loop (blocks 317-333). The system 200 calculates the longitudinal and rotational coordinates of the needle guide assembly based on the particular geometry and position of the current needle path. As discussed above, the system 200 derives the needle paths from the specific biopsy pattern selected at block 311 and the spatial attributes entered by the operator at blocks 303 and 305, and uses this data in conjunction with various reference coordinate systems and transformations therebetween to derive the longitudinal and rotational coordinates of the needle guide assembly 111. In the preferred embodiment, the software logic of the data processing system 200 may display specific mechanical adjustment settings of the guide assembly 111 which place the guide assembly 111 at the proper position and orientation for the current needle path. In the preferred embodiment, when adjusting the probe 10, an operator may make relatively large changes to the probe depth in the patient by adjusting a depth scale coupled to a proximal end of the probe, and may make relatively small changes to the depth of the probe (e.g., less than ten millimeters) with a fine tuning knob or dial, also disposed at the proximal end of the probe. In the preferred embodiment, the operator may also adjust the angular position of the guide assembly 111 by adjusting a collar scale coupled to the guide/index collar 189. It is also envisioned that the adjustment of the probe 10, guide/index collar 189 and guide assembly 111 could be controlled automatically by motorized adjustment under control of the data processing system 200.

In optional block 329, the operations of block 319 to 323 as described above can be repeated to verify there is no patient movement after movement of the guide assembly in block 327.

In block 331, the operator procures a biopsy sample by inserting the needle assembly through the needle guide assembly 111, which directs the needle assembly along the corresponding needle path. Under control of the operator, the biopsy gun is fired, which causes the needle assembly to pass through the wall of the rectum into the prostate and capture a tissue sample at the target location of the prostate. Ultrasound image(s) may optionally be scanned and saved to the hard disk during procurement of the biopsy sample to create a permanent record of the biopsy tissue location, depth of penetration of the needle assembly, etc. associated with the needle path of the particular sample. The operator then removes the needle assembly containing the captured tissue sample from the needle guide assembly 111 and places the captured tissue sample into a tissue specimen dish.

At block 333, the system 200 evaluates whether or not all of the samples of the biopsy plan have been procured. If so, then loop of blocks 317 to 333 ends. Otherwise, the operations return to block 317 to procure the next sample of the biopsy plan.

It will be appreciated that the system and methodology of the present invention allows for all of the biopsy samples of the biopsy plan to be taken from the prostate while visually monitoring real time spatial attributes of feature(s) of the prostate relative to previously inputted operator-marked spatial attribute(s) of the feature(s). In this manner, the operator can adjust for patient movement between samples and better adhere to the desired biopsy plan of sampling the prostate in specifically targeted areas.

It will also be appreciated that the needle paths of the biopsy plan may intersect, lie within, or be parallel to the predefined image planes depending on the type of probe and delivery system utilized, the nature of the biopsy plan, the specific areas of the prostate for which biopsy samples are desired, and the feasibility of reaching and viewing those areas.

The system of the present invention can be used to detect patient movement during the delivery of treatment to localized areas (typically referred to as "target sites") of the prostate. In such a system, the guide assembly 111 of the system is rotatively and longitudinally positioned atop the probe such that it guides a flexible cannula (or other elongate flexible instrument) transrectally along a path leading to the respective target site. The distal tip of the flexible instrument is positioned at the respective target side for application of the localized treatment to the target site. The system and method of the present invention as described herein can be used to visually detect patient movement before treatment is applied to a respective target site. The treatment applied to the target site can take many forms, including but not limited to:

placement of gold or other forms of markers at the target site;
placement of one or more cryotherapy probes at the target site;
placement of one or more brachytherapy seeds at the target site;
delivery of laser therapy (or other forms of radiation therapy) to the target site;
delivery of drugs to the target site; and
delivery of other forms of therapy including heat and vapors to the target site.

Brachytherapy is a minimally invasive treatment that administers radioactive seeds (the size of a grain of rice) directly into the prostate, which allows the ability to use higher doses in the seeds without damaging any surrounding healthy tissue. The radioactive seeds are placed into thin needles and directed into the prostate through the perineum. The seeds release low dose radiation for several weeks or months, killing the cancer cells. Cryotherapy uses argon gas to freeze and helium gas to thaw, a process which destroys cancer cells in the prostate. A warming catheter is inserted through the urethra to protect it during the freezing process of the prostate. The cancer cells in the prostate are destroyed as they thaw.

Various biopsy guns, needles, cannulas, delivery mechanisms, and guide assemblies may also be utilized in conjunction with the improved probe 10. The improved ultrasonic probe may also be used to provide guidance during transperineal procedures, including brachytherapy, cryotherapy, or other transperineal saturation biopsies in which the needle is inserted through a grid through the perineum and transrectal images from the probe are used for guidance.

The probe may also be used for guidance during laparoscopic and non-laparoscopic surgeries involving other cavities such as the abdominal cavity (e.g., surgeries involving the small intestine, large intestine, stomach, spleen, liver, pancreas, kidneys, and adrenal glands), the thoracic cavity, and the pelvic cavity, or during surgeries involving other tissue or joints in the body.

There have been described and illustrated herein several embodiments of an ultrasonic imaging probe, data processing system, and methods associated therewith for detecting movement of a patient during a surgical procedure that acts on target tissue imaged by the imaging probe. While particular embodiments of the invention have been described, it is not intended that the invention be limited thereto, as it is intended that the invention be as broad in scope as the art will allow and that the specification be read likewise. Thus, while a particular ultrasonic imaging system is described, other suitable ultrasonic imaging systems can be used. Moreover, other forms of medical imaging can be used, which can include, but are not limited to, projection radiography and fluoroscopy systems, magnetic resonance imaging (MRI) systems, computed axial tomography (CAT) systems, positron emission tomography (PET) systems, scintigraphy systems, and other suitable medical imaging systems. Moreover, while particular configurations of a needle cannula, guide assembly, biopsy deliver system which includes an improved probe and a biopsy gun, and a data processing system have been disclosed, it will be appreciated that other configurations may be utilized. Also, while the needle, cannula, and improved probe have been disclosed for biopsying the prostate of a patient, it will be recognized that the needle, cannula, and improved probe can be used for biopsying tissue of other organs or other parts of the body and that the improved probe may be inserted through other cavities in the body and utilized for guiding other procedures such as brachytherapy, cryotherapy and saturation biopsies. It will also be appreciated that while a method for procuring biopsy samples in the prostate and for detecting movement of the patient relative to a transrectal probe has been disclosed, the method may be used for other targeted tissue within or adjacent a body cavity of the patient. While specific method steps have been disclosed for detecting movement of the patient relative to the probe, it will be appreciated that one or more of these steps may be eliminated or re-ordered. In addition, while a particular data processing system has been disclosed, other data processing systems may be utilized. It therefore will be appreciated by those skilled in the art that yet other modifications could be made to the provided mention without deviating from its spirit and scope as claimed.

What is claimed is:

1. A method for detecting movement of a patient relative to an imaging device that generates images of target tissue of a patient for a surgical procedure, the method comprising the steps of:
   capturing by an imaging device located in a body cavity of a patient first image data along a scan plane passing through the target tissue, the capturing of the first image data being performed independent of and not in relation to a specific reference point on the target tissue;
   displaying the first image data as a first image of the target tissue on a display device;
   identifying at least one spatial attribute of the target tissue in the displayed first image from the captured first image data as an identified spatial attribute, each identified spatial attribute being a feature of the target tissue, each identified spatial attribute being determined independently from and without reference to the imaging device or any other reference structure apart from the target tissue, each identified spatial attribute being determined based on the displayed first image independent from the surgical procedure;
   storing data corresponding to a position of each identified spatial attribute determined in relation to the first image;
   capturing by the imaging device second image data of the target tissue along the scan plane passing through the target tissue, the capturing of the second image data being performed independent of and not in relation to a specific reference point on the target tissue;
   displaying the second image data as a second image of the target tissue on the display device in conjunction with displaying a visual indicator for each identified spatial attribute, wherein a position of each visual indicator displayed in conjunction with the second image on the display device is displayed at a position dictated by the stored data corresponding to a respective position of each identified spatial attribute determined in relation to the first image; and
   comparing the position of each visual indicator determined in relation to the first image displayed on the display device with a position of a corresponding identified spatial attribute of the target tissue of the second image to detect a shift in the position of each identified spatial attribute of the target tissue indicating movement of the patient prior to and during the procedure.

2. The method according to claim 1, wherein:
   the procedure acts on a sequence of localized portions of the target tissue, and the second image data is captured by the imaging device and displayed on the display device prior to acting on each respective localized portion of the target tissue.

3. The method according to claim 1, wherein:
   the procedure comprises one or more of a biopsy procedure that extracts a sample of the target tissue or a procedure that applies a treatment to the target tissue.

4. The method according to claim 1, the method further comprising the step of:
   displaying with the first image on the display device each visual indicator at a position corresponding to the respective position of each identified spatial attribute determined in relation to the first image.

5. The method according to claim 1, wherein the procedure applies a treatment to the target tissue and the treatment is selected from the group consisting of:
   placement of gold or other forms of markers in the target tissue;
   placement of one or more cryotherapy probes in the target tissue;
   placement of one or more brachytherapy seeds in the target tissue;
   delivery of laser therapy or other forms of radiation therapy to the target tissue;
   delivery of drugs to the target tissue;
   placement of biopsy needles in the target tissue; and
   delivery of therapy to the target tissue.

6. The method according to claim 1, wherein:
   the imaging device comprises an elongate probe for insertion into the body cavity of the patient.

7. The method according to claim 1, wherein:
   the target tissue comprises a prostate of the patient, and
   the imaging device comprises an elongate ultrasonic imaging probe for insertion into a rectum of the patient.

8. The method according to claim 7, wherein:
   the target tissue is acted upon by a flexible surgical instrument that is advanced transrectally to the target tissue of the prostate of the patient.

9. The method according to claim 8, wherein:
   positioning of the flexible surgical instrument is guided by a guide assembly mounted atop the elongate ultrasonic imaging probe.

10. The method according to claim 9, wherein:
    the elongate ultrasonic imaging probe has a central axis, and
    the guide assembly is rotatable about the central axis relative to the elongate ultrasonic imaging probe and moveable along an axis parallel to the central axis relative to the elongate ultrasonic imaging probe.

11. The method according to claim 10, wherein:
    the guide assembly includes a guide body that defines a guide channel for guiding, positioning and orienting the flexible surgical instrument passing therethrough and exiting therefrom.

12. The method according to claim 11, wherein:
    the guide assembly provides manual indexed adjustment of rotation of the guide body about the central axis relative to the elongate ultrasonic imaging probe, and
    the guide assembly provides manual indexed movement of the guide body along the axis parallel to the central axis relative to the elongate ultrasonic imaging probe.

13. The method according to claim 11, wherein:
    the second image data is captured by the imaging device and displayed on the display device and, when movement of the patient is not detected, the guide assembly is positioned such that the guide channel guides, positions and orients the flexible surgical instrument pass-

27 ing therethrough and exiting therefrom in order to act on a localized portion of the target tissue.

14. The method according to claim 1, wherein:
the display device includes a touch-screen input for inputting information from an operator.

15. The method according to claim 14, wherein:
the information input from the operator includes at least one operator-identified feature of the target tissue, the at least one operator-identified feature corresponding to the at least one identified spatial attribute within the first image of the target tissue.

16. The method according to claim 1, wherein:
the target tissue is a prostate of the patient and the at least one identified spatial attribute of the target tissue includes at least one of a base and an apex of the prostate of the patient.

17. The method according to claim 1, wherein:
the visual indicator is a vertical line.

18. The method according to claim 1, wherein:
the visual indicator is an icon.

19. A surgical system for detecting movement of a patient, comprising:
an imaging device configured to capture images of a target tissue of a patient prior to and during a surgical procedure, the imaging device being configured to capture first image data and to capture second image data along a scan plane passing through the target tissue, the imaging device configured to capture the first image data and the second image data independent of and not in relation to a specific reference point on the target tissue;
a display device configured to display the first image data as a first image, to display the second image data as a second image and to display a visual indicator at each position corresponding to a location of an identified spatial attribute of the target tissue, each identified spatial attribute being a feature of the target tissue, each identified spatial attribute being determined in the displayed first image from the captured first image data independently from and without reference to the imaging device or any other reference structure apart from the target tissue, each identified spatial attribute being determined based on the displayed first image independent from the surgical procedure;
an input device for inputting information from an operator of the surgical system; and
a data processing apparatus having a data storage medium, wherein:
the data processing apparatus is operably coupled to the imaging device and is configured to control the imaging device to capture the first image data along the scan plane passing through the target tissue and to control the display device to display the first image data as the first image on the display device,
the data processing apparatus is configured to identify, based on input information from the input device, each identified spatial attribute of the target tissue,
the data processing apparatus is configured to store data in the data storage medium corresponding to a respective position of each identified spatial attribute determined in relation to the first image,
the data processing apparatus is configured to control the imaging device to capture the second image data along the scan plane passing through the target tissue, and
the data processing apparatus is configured to control the display device to display on the display device the second image of the target tissue in conjunction with displaying on the display device the visual indicator for each identified spatial attribute at the respective position corresponding to the position of each identified spatial attribute determined in relation to the first image, and
wherein the position of each visual indicator determined in relation to the first image displayed on the display device in relation to a position of a corresponding identified spatial attribute of the target tissue of the second image displayed on the display device indicates whether a shift in the position of each identified spatial attribute of the target tissue has occurred, the shift in position indicating movement of the patient prior to and during a procedure.

20. The surgical system for detecting movement of a patient according to claim 19, wherein:
the imaging device comprises an elongate ultrasonic imaging probe for insertion into a body cavity of the patient.

21. The surgical system for detecting movement of a patient according to claim 20, wherein:
the elongate ultrasonic imaging probe has a central axis, and
the elongate ultrasonic imaging probe comprises a guide assembly mounted atop the elongate ultrasonic imaging probe, the guide assembly configured to guide and position a flexible instrument for the procedure.

22. The surgical system for detecting movement of a patient according to claim 21, wherein:
the guide assembly is rotatable about the central axis relative to the elongate ultrasonic imaging probe and moveable along an axis parallel to the central axis relative to the elongate ultrasonic imaging probe.

23. The surgical system for detecting movement of a patient according to claim 21, wherein:
the guide assembly includes a guide body that defines a guide channel configured to guide, position and orient the flexible instrument passing therethrough and exiting therefrom in order to act on the target tissue.

24. The surgical system for detecting movement of a patient according to claim 19, wherein:
the visual indicator is a vertical line.

25. The surgical system for detecting movement of a patient according to claim 19, wherein:
the visual indicator is an icon.

26. The surgical system for detecting movement of a patient according to claim 19, wherein:
the target tissue is a prostate of the patient, and
at least one identified spatial attribute of the target tissue includes at least one of a base and an apex of the prostate of the patient.

27. The surgical system for detecting movement of a patient according to claim 26, wherein:
the imaging device comprises an elongate ultrasonic imaging probe for insertion into a body cavity of the patient.

28. The surgical system for detecting movement of a patient according to claim 19, wherein:
the data processing apparatus is configured to control the display device to display the first image and to display each visual indicator in conjunction with the first image at the respective position of each identified spatial attribute of the target tissue determined in relation to the first image.

* * * * *